(12) United States Patent
Hinnah et al.

(10) Patent No.: US 7,867,707 B2
(45) Date of Patent: Jan. 11, 2011

(54) METHOD FOR DETECTING ANALYTES IN A SAMPLE

(75) Inventors: Silke Christine Hinnah, Hamburg (DE); Dagmar Lambrü, Fassberg (DE); Sonja Dröge, Elmshorn (DE); Stefan Jäger, Hamburg (DE); Karsten Gall, Lunestedt (DE); Werner Stürmer, Constance (DE); Michaela Schäfer, Constance (DE)

(73) Assignee: Evotec AG, Hamburg (DE)

( * ) Notice: Subject to any disclaimer, the term of this patent is extended or adjusted under 35 U.S.C. 154(b) by 456 days.

(21) Appl. No.: 11/629,107

(22) PCT Filed: Jun. 11, 2004

(86) PCT No.: PCT/EP2004/006344

§ 371 (c)(1),
(2), (4) Date: Jul. 11, 2008

(87) PCT Pub. No.: WO2005/121359

PCT Pub. Date: Dec. 22, 2005

(65) Prior Publication Data

US 2009/0325186 A1   Dec. 31, 2009

(51) Int. Cl.
*C12Q 1/68* (2006.01)
*C07H 21/02* (2006.01)
*C07H 21/04* (2006.01)

(52) U.S. Cl. .......................... 435/6; 536/23.1; 536/24.3
(58) Field of Classification Search ................ 435/6; 536/23.1, 24.3
See application file for complete search history.

(56) References Cited

U.S. PATENT DOCUMENTS

| 5,091,652 A | * | 2/1992 | Mathies et al. ............ 250/458.1 |
| 5,252,459 A | * | 10/1993 | Tarcha et al. .................. 435/6 |
| 5,639,609 A | * | 6/1997 | Kruse-Mueller et al. ....... 435/6 |
| 6,410,231 B1 | * | 6/2002 | Arnold et al. .................. 435/6 |
| 6,447,995 B1 | * | 9/2002 | Carrion et al. ................. 435/5 |
| 6,495,324 B1 | | 12/2002 | Mirkin et al. |
| 2004/0053256 A1 | | 3/2004 | Lee et al. |

FOREIGN PATENT DOCUMENTS

| EP | 0 851 228 A1 | 7/1998 |
| EP | 1 431 398 A1 | 7/1998 |
| WO | WO 90/01564 A | 2/1990 |
| WO | WO 00/50869 | 8/2000 |
| WO | WO 2004/057023 A1 | 7/2004 |

OTHER PUBLICATIONS

Kawamura et al., Confocal Laser Microscope Scanner and CCD Camera. Yokogawa Technical Report No. 33 pp. 17-20.*
Kohara, Yoshinobu et al., "DNA probes on beads arrayed in a capillary, 'Bead-array', exhibited high Hybridization performance," Nucleic Acids Research, Aug. 15, 2002, vol. 30 No. 16 pp. e87-e87-7
Clarke, A. Paul et al., "Gene expression microarray analysis in cancer biology, pharmacology, and drug development: progress and potential," Biochemical Pharmacology, Nov. 15. 2001, vol. 62, No. 10, pp. 1311-1336.
Spiro, Alexander et al., "A Bead-Based Method for Multiplexed Identification and Quantitation of DNA Sequences Using Flow Cytometry," Applied and Environmental Microbiology, Oct. 2000, vol. 66, No. 10, pp. 4258-4265.

* cited by examiner

*Primary Examiner*—Ethan Whisenant
(74) *Attorney, Agent, or Firm*—Jacobson Holman PLLC

(57) ABSTRACT

The present invention relates to a method for detecting analytes in a sample comprising the steps of
   providing a solid support,
   providing capture probes being bound or capable of binding to the solid support, which capture probes are also capable of binding to the analytes, thus concentrating the analytes on the solid support,
   providing detection probes which are capable of binding to the analytes,
   contacting the sample with the detection probes, the solid support and the capture probes, and
   detecting through use of confocal observation the analytes which are bound to the detection probes.

33 Claims, 9 Drawing Sheets

SEQUENCE LISTING

<160> NUMBER OF SEQ ID NOS: 106

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence:capture
      oligonucleotide for the detection of c-fos mRNA

<400> SEQUENCE: 1
ggctctggtc tgcgatggg                                              19

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:capture
      oligonucleotide for the detection of c-fos mRNA

<400> SEQUENCE: 2

```
gggactccga aagggtgagg                                          20
```

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:capture
      oligonucleotide for the detection of c-fos mRNA

<400> SEQUENCE: 3

```
cctttctct tcttcttctg gagataa                                   27
```

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:capture
      oligonucleotide for the detection of c-fos mRNA

<400> SEQUENCE: 4

```
attcctttcc cttcggattc t                                        21
```

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:capture
      oligonucleotide for the detection of c-fos mRNA

<400> SEQUENCE: 5

```
atctcggtct gcaaagcaga c                                        21
```

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:capture
      oligonucleotide for the detection of c-fos mRNA

<400> SEQUENCE: 6

```
tctccttcag caggttggca                                          20
```

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:capture
      oligonucleotide for the detection of c-fos mRNA

<400> SEQUENCE: 7

```
ccacagacat ctcttctggg aag                                      23
```

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:capture
      oligonucleotide for the detection of c-fos mRNA

<400> SEQUENCE: 8

```
ccccagtcag atcaagggaa g                                        21
```

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence:detection
      oligonucleotide for the detection of c-fos mRNA

<400> SEQUENCE: 9
atgaagttgg cactggagac gg                                        22

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence:detection
      oligonucleotide for the detection of c-fos mRNA

<400> SEQUENCE: 10
atggcagtga ccgtggga                                             18

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence:detection
      oligonucleotide for the detection of c-fos mRNA

<400> SEQUENCE: 11
caggtccgga ctggtcgag                                            19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence:detection
      oligonucleotide for the detection of c-fos mRNA

<400> SEQUENCE: 12
cgggctgcac cagccactg                                            19

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence:detection
      oligonucleotide for the detection of c-fos mRNA

<400> SEQUENCE: 13
ccagccctgg agtaagcc                                             18

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence:detection
      oligonucleotide for the detection of c-fos mRNA

<400> SEQUENCE: 14
ctcctgtcat ggtcttcaca acg                                       23

```
<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence:detection
      oligonucleotide for the detection of c-fos mRNA

<400> SEQUENCE: 15
ccaatgctct gcgctcggc                                               19

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence:detection
      oligonucleotide for the detection of c-fos mRNA

<400> SEQUENCE: 16
ctgttccacc ttgcccctcc tg                                           22

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence:detection
      oligonucleotide for the detection of c-fos mRNA

<400> SEQUENCE: 17
ccctcctccg gttgcgg                                                 17

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence:detection
      oligonucleotide for the detection of c-fos mRNA

<400> SEQUENCE: 18
cgcttggagt gtatcagtca gct                                          23

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence:detection
      oligonucleotide for the detection of c-fos mRNA

<400> SEQUENCE: 19
ccaggatgaa ctctagtttt tcct                                         24

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence:detection
      oligonucleotide for the detection of c-fos mRNA

<400> SEQUENCE: 20
caggcaggtc ggtgagctg                                               19
```

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence:detection
      oligonucleotide for the detection of c-fos mRNA

<400> SEQUENCE: 21
cccaggtcat cagggatctt g                                              21

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:detection
      oligonucleotide for the detection of c-fos mRNA

<400> SEQUENCE: 22
aggcctcctc agactccggg                                                20

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence:detection
      oligonucleotide for the detection of c-fos mRNA

<400> SEQUENCE: 23
tgaggagagg cagggtga                                                  18

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence:detection
      oligonucleotide for the detection of c-fos mRNA

<400> SEQUENCE: 24
agggcttggg ctcagggtca t                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence:detection
      oligonucleotide for the detection of c-fos mRNA

<400> SEQUENCE: 25
tgctcttgac aggttccact g                                              21

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:detection
      oligonucleotide for the detection of c-fos mRNA

<400> SEQUENCE: 26
aagtcatcaa agggctcggt                                                20

<210> SEQ ID NO 27

```
<211> LENGTH: 22
<212> TYPE: DNA
<213> ORGANISM: Artificial Sequence
<220> FEATURE:
<223> OTHER INFORMATION: Description of Artificial Sequence:detection
      oligonucleotide for the detection of c-fos mRNA

<400> SEQUENCE: 27
cctggatgat gctgggaaca gg                                              22

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence:unlabeled
      oligonucleotide for the detection of c-fos mRNA

<400> SEQUENCE: 28
gccacagagg agacgaggg                                                  19

<210> SEQ ID NO 29
<211> LENGTH: 15
<212> TYPE: DNA
<213> ORGANISM: Artificial Sequence
<220> FEATURE:
<223> OTHER INFORMATION: Description of Artificial Sequence:unlabeled
      oligonucleotide for the detection of c-fos mRNA

<400> SEQUENCE: 29
ccagcggagg gggcg                                                      15

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence:unlabeled
      oligonucleotide for the detection of c-fos mRNA

<400> SEQUENCE: 30
catttggctg cagccatctt                                                 20

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence:unlabeled
      oligonucleotide for the detection of c-fos mRNA

<400> SEQUENCE: 31
ttctcatctt ctagttggtc tgtctc                                          26

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence:unlabeled
      oligonucleotide for the detection of c-fos mRNA

<400> SEQUENCE: 32
gtggcaacct ctggcaggc                                                  19

<210> SEQ ID NO 33
<211> LENGTH: 20
```

```
<212> TYPE: DNA
<213> ORGANISM: Artificial Sequence
<220> FEATURE:
<223> OTHER INFORMATION: Description of Artificial Sequence:unlabeled
      oligonucleotide for the detection of c-fos mRNA

<400> SEQUENCE: 33
cttcagctcc atgctgctga                                              20

<210> SEQ ID NO 34
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of c-fos mRNA

<400> SEQUENCE: 34
cagtgccaac ttcat                                                   15

<210> SEQ ID NO 35
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of c-fos mRNA

<400> SEQUENCE: 35
cacggtcact gccat                                                   15

<210> SEQ ID NO 36
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of c-fos mRNA

<400> SEQUENCE: 36
accagtccgg acctg                                                   15

<210> SEQ ID NO 37
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of c-fos mRNA

<400> SEQUENCE: 37
ggctggtgca gcccg                                                   15

<210> SEQ ID NO 38
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of c-fos mRNA

<400> SEQUENCE: 38
ttactccagg gctgg                                                   15

<210> SEQ ID NO 39
<211> LENGTH: 15
<212> TYPE: DNA
```

```
<213> ORGANISM: Artificial Sequence
<220> FEATURE:
<223> OTHER INFORMATION: Description of Artificial Sequence:FRET
      quencher oligonucleotide for the detection of c-fos mRNA

<400> SEQUENCE: 39
agaccatgac aggag                                              15

<210> SEQ ID NO 40
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of c-fos mRNA

<400> SEQUENCE: 40
agcgcagagc attgg                                              15

<210> SEQ ID NO 41
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of c-fos mRNA

<400> SEQUENCE: 41
ggcaaggtgg aacag                                              15

<210> SEQ ID NO 42
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of c-fos mRNA

<400> SEQUENCE: 42
gcaaccggag gaggg                                              15

<210> SEQ ID NO 43
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of c-fos mRNA

<400> SEQUENCE: 43
gatacactcc aagcg                                              15

<210> SEQ ID NO 44
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of c-fos mRNA

<400> SEQUENCE: 44
tagagttcat cctgg                                              15

<210> SEQ ID NO 45
<211> LENGTH: 15
<212> TYPE: DNA
<213> ORGANISM: Artificial Sequence
```

```
<220> FEATURE:
<223> OTHER INFORMATION: Description of Artificial Sequence:FRET
      quencher oligonucleotide for the detection of c-fos mRNA

<400> SEQUENCE: 45
tcaccgacct gcctg                                                     15

<210> SEQ ID NO 46
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of c-fos mRNA

<400> SEQUENCE: 46
ccctgatgac ctggg                                                     15

<210> SEQ ID NO 47
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of c-fos mRNA

<400> SEQUENCE: 47
agtctgagga ggcct                                                     15

<210> SEQ ID NO 48
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of c-fos mRNA

<400> SEQUENCE: 48
ccctgcctct cctca                                                     15

<210> SEQ ID NO 49
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of c-fos mRNA

<400> SEQUENCE: 49
ctgagcccaa gccct                                                     15

<210> SEQ ID NO 50
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of c-fos mRNA

<400> SEQUENCE: 50
aacctgtcaa gagca                                                     15

<210> SEQ ID NO 51
<211> LENGTH: 15
<212> TYPE: DNA
<213> ORGANISM: Artificial Sequence
<220> FEATURE:
```

<223> OTHER INFORMATION: Description of Artificial Sequence:FRET
      quencher oligonucleotide for the detection of c-fos mRNA

<400> SEQUENCE: 51
gccctttgat gactt                                                    15

<210> SEQ ID NO 52
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of c-fos mRNA

<400> SEQUENCE: 52
ccagcatcat ccagg                                                    15

<210> SEQ ID NO 53
<211> LENGTH: 26
<212> TYPE: DNA
<213> ORGANISM: Artificial Sequence
<220> FEATURE:
<223> OTHER INFORMATION: Description of Artificial Sequence:primer for
      c-fos mRNA

<400> SEQUENCE: 53
gcgaattcct cgggcttcaa cgcaga                                        26

<210> SEQ ID NO 54
<211> LENGTH: 25
<212> TYPE: DNA
<213> ORGANISM: Artificial Sequence
<220> FEATURE:
<223> OTHER INFORMATION: Description of Artificial Sequence:primer for
      c-fos mRNA

<400> SEQUENCE: 54
atggatccca gcgtgggtga gctga                                         25

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence:capture
      oligonucleotide for the detection of cyp1A1 mRNA

<400> SEQUENCE: 55
ctgcaacgtg cttatcagga c                                             21

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence:capture
      oligonucleotide for the detection of cyp1A1 mRNA

<400> SEQUENCE: 56
caggccctgc catcagctc                                                19

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence:capture oligonucleotide for the detection of cyp1A1 mRNA

<400> SEQUENCE: 57
ttgactaggc taagcagttc ttgg                                          24

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence:capture
      oligonucleotide for the detection of cyp1A1 mRNA

<400> SEQUENCE: 58
cctccccgaa attattattc agg                                           23

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence:capture
      oligonucleotide for the detection of cyp1A1 mRNA

<400> SEQUENCE: 59
cattcaggtc cttgaaggca tt                                            22

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence:capture
      oligonucleotide for the detection of cyp1A1 mRNA

<400> SEQUENCE: 60
ttctgcatga agctgtagaa cttct                                         25

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence:capture
      oligonucleotide for the detection of cyp1A1 mRNA

<400> SEQUENCE: 61
gttcatcacc aaatacatga gg                                            22

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence:capture
      oligonucleotide for the detection of cyp1A1 mRNA

<400> SEQUENCE: 62
ccaatcactg tgtctagctc ctc                                           23

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence:detection
      oligonucleotide for the detection of cyp1A1 mRNA

<400> SEQUENCE: 63
ccattctggg ccaggcgc                                                          18

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence:detection
      oligonucleotide for the detection of cyp1A1 mRNA

<400> SEQUENCE: 64
aggcaatgga gaaactttc agg                                                    23

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence:detection
      oligonucleotide for the detection of cyp1A1 mRNA

<400> SEQUENCE: 65
ttgaggaggc tgggtcag                                                          18

<210> SEQ ID NO 66
<211> LENGTH: 22
<212> TYPE: DNA
<213> ORGANISM: Artificial Sequence
<220> FEATURE:
<223> OTHER INFORMATION: Description of Artificial Sequence:detection
      oligonucleotide for the detection of cyp1A1 mRNA

<400> SEQUENCE: 66
tgctcttcca ggtagcagga gg                                                     22

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence:detection
      oligonucleotide for the detection of cyp1A1 mRNA

<400> SEQUENCE: 67
tgacattggt cactgatacc acc                                                    23

<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence:detection
      oligonucleotide for the detection of cyp1A1 mRNA

<400> SEQUENCE: 68
ccaaagcaaa tggcacaga                                                         19

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence:detection
      oligonucleotide for the detection of cyp1A1 mRNA -continued

```
<400> SEQUENCE: 69
tggttgtggt catagcgccg g                                              21

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence:detection
      oligonucleotide for the detection of cyp1A1 mRNA

<400> SEQUENCE: 70
tgggtttcca gagccaacca                                                20

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence:detection
      oligonucleotide for the detection of cyp1A1 mRNA

<400> SEQUENCE: 71
cgaagaatag ggatgaactc agc                                            23

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence:detection
      oligonucleotide for the detection of cyp1A1 mRNA

<400> SEQUENCE: 72
cagggaaggg ttgggtaggt ag                                             22

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence:detection
      oligonucleotide for the detection of cyp1A1 mRNA

<400> SEQUENCE: 73
ttttgtagtg ctccttgacc atc                                            23

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence:detection
      oligonucleotide for the detection of cyp1A1 mRNA

<400> SEQUENCE: 74
atgtggccct tctcaaagg                                                 19

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence:detection
      oligonucleotide for the detection of cyp1A1 mRNA

<400> SEQUENCE: 75
```

```
tcaggctgtc tgtgatgtcc cgg                                          23
```

<210> SEQ ID NO 76
<211> LENGTH: 22
<212> TYPE: DNA
<213> ORGANISM: Artificial Sequence
<220> FEATURE:
<223> OTHER INFORMATION: Description of Artificial Sequence:detection
      oligonucleotide for the detection of cyp1A1 mRNA

<400> SEQUENCE: 76

```
tgcttctcct gacagtgctc aa                                           22
```

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence:detection
      oligonucleotide for the detection of cyp1A1 mRNA

<400> SEQUENCE: 77

```
cattggcgtt ctcatccagc                                              20
```

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence:detection
      oligonucleotide for the detection of cyp1A1 mRNA

<400> SEQUENCE: 78

```
tgatcttctc atctgacagc tgga                                         24
```

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence:detection
      oligonucleotide for the detection of cyp1A1 mRNA

<400> SEQUENCE: 79

```
caaagaggtc caagacgatg ttaa                                         24
```

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence:detection
      oligonucleotide for the detection of cyp1A1 mRNA

<400> SEQUENCE: 80

```
tgactgtgtc aaacccagct c                                            21
```

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence:detection
      oligonucleotide for the detection of cyp1A1 mRNA

<400> SEQUENCE: 81
ttggatcttt ctctgtaccc tggg       24

<210> SEQ ID NO 82
<211> LENGTH: 22
<212> TYPE: DNA
<213> ORGANISM: Artificial Sequence
<220> FEATURE:
<223> OTHER INFORMATION: Description of Artificial Sequence:detection
      oligonucleotide for the detection of cyp1A1 mRNA

<400> SEQUENCE: 82
tgggatctgt cagagagccg gg       22

<210> SEQ ID NO 83
<211> LENGTH: 19
<212> TYPE: DNA
<213> ORGANISM: Artificial Sequence
<220> FEATURE:
<223> OTHER INFORMATION: Description of Artificial Sequence:unlabeled
      oligonucleotide for the detection of cyp1A1 mRNA

<400> SEQUENCE: 83
ctcagcctcc ttgctcaca       19

<210> SEQ ID NO 84
<211> LENGTH: 25
<212> TYPE: DNA
<213> ORGANISM: Artificial Sequence
<220> FEATURE:
<223> OTHER INFORMATION: Description of Artificial Sequence:unlabeled
      oligonucleotide for the detection of cyp1A1 mRNA

<400> SEQUENCE: 84
acatacctgt aggggttaaa gtgcc       25

<210> SEQ ID NO 85
<211> LENGTH: 19
<212> TYPE: DNA
<213> ORGANISM: Artificial Sequence
<220> FEATURE:
<223> OTHER INFORMATION: Description of Artificial Sequence:unlabeled
      oligonucleotide for the detection of cyp1A1 mRNA

<400> SEQUENCE: 85
ctccaggaga tagcagttg       19

<210> SEQ ID NO 86
<211> LENGTH: 14
<212> TYPE: DNA
<213> ORGANISM: Artificial Sequence
<220> FEATURE:
<223> OTHER INFORMATION: Description of Artificial Sequence:unlabeled
      oligonucleotide for the detection of cyp1A1 mRNA

<400> SEQUENCE: 86
gccgccgtga cctg       14

<210> SEQ ID NO 87
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of cyp1A1 mRNA

<400> SEQUENCE: 87
cctggcccag aatgg       15

<210> SEQ ID NO 88
<211> LENGTH: 15
<212> TYPE: DNA
<213> ORGANISM: Artificial Sequence
<220> FEATURE:
<223> OTHER INFORMATION: Description of Artificial Sequence:FRET quencher oligonucleotide for the detection of cyp1A1 mRNA

<400> SEQUENCE: 88
gtttctccat tgcct                                                        15

<210> SEQ ID NO 89
<211> LENGTH: 15
<212> TYPE: DNA
<213> ORGANISM: Artificial Sequence
<220> FEATURE:
<223> OTHER INFORMATION: Description of Artificial Sequence:FRET quencher oligonucleotide for the detection of cyp1A1 mRNA

<400> SEQUENCE: 89
acccagcctc ctcaa                                                        15

<210> SEQ ID NO 90
<211> LENGTH: 15
<212> TYPE: DNA
<213> ORGANISM: Artificial Sequence
<220> FEATURE:
<223> OTHER INFORMATION: Description of Artificial Sequence:FRET quencher oligonucleotide for the detection of cyp1A1 mRNA

<400> SEQUENCE: 90
ctacctggaa gagca                                                        15

<210> SEQ ID NO 91
<211> LENGTH: 15
<212> TYPE: DNA
<213> ORGANISM: Artificial Sequence
<220> FEATURE:
<223> OTHER INFORMATION: Description of Artificial Sequence:FRET quencher oligonucleotide for the detection of cyp1A1 mRNA

<400> SEQUENCE: 91
cagtgaccaa tgtca                                                        15

<210> SEQ ID NO 92
<211> LENGTH: 15
<212> TYPE: DNA
<213> ORGANISM: Artificial Sequence
<220> FEATURE:
<223> OTHER INFORMATION: Description of Artificial Sequence:FRET quencher oligonucleotide for the detection of cyp1A1 mRNA

<400> SEQUENCE: 92
tgccatttgc tttgg                                                        15

<210> SEQ ID NO 93
<211> LENGTH: 15
<212> TYPE: DNA
<213> ORGANISM: Artificial Sequence
<220> FEATURE:
<223> OTHER INFORMATION: Description of Artificial Sequence:FRET quencher oligonucleotide for the detection of cyp1A1 mRNA

<400> SEQUENCE: 93
ctatgaccac aacca                                                        15

```
<210> SEQ ID NO 94
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of cyp1A1 mRNA

<400> SEQUENCE: 94
ggctctggaa accca                                                    15

<210> SEQ ID NO 95
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of cyp1A1 mRNA

<400> SEQUENCE: 95
catccctatt cttcg                                                    15

<210> SEQ ID NO 96
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of cyp1A1 mRNA

<400> SEQUENCE: 96
cccaacccct ccctg                                                    15

<210> SEQ ID NO 97
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of cyp1A1 mRNA

<400> SEQUENCE: 97
aggagcacta caaaa                                                    15

<210> SEQ ID NO 98
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of cyp1A1 mRNA

<400> SEQUENCE: 98
tgagaagggc cacat                                                    15

<210> SEQ ID NO 99
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of cyp1A1 mRNA

<400> SEQUENCE: 99
tcacagacag cctga                                                    15
```

```
<210> SEQ ID NO 100
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of cyp1A1 mRNA

<400> SEQUENCE: 100
ctgtcaggag aagca                                                    15

<210> SEQ ID NO 101
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of cyp1A1 mRNA

<400> SEQUENCE: 101
atgagaacgc caatg                                                    15

<210> SEQ ID NO 102
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of cyp1A1 mRNA

<400> SEQUENCE: 102
cagatgagaa gatca                                                    15

<210> SEQ ID NO 103
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of cyp1A1 mRNA

<400> SEQUENCE: 103
tcttggacct ctttg                                                    15

<210> SEQ ID NO 104
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of cyp1A1 mRNA

<400> SEQUENCE: 104
ggtttgacac agtca                                                    15

<210> SEQ ID NO 105
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of cyp1A1 mRNA

<400> SEQUENCE: 105
cagagaaaga tccaa                                                    15

<210> SEQ ID NO 106
```

-continued

```
<211> LENGTH: 15
<212> TYPE: DNA
<213> ORGANISM: Artificial Sequence
<220> FEATURE:
<223> OTHER INFORMATION: Description of Artificial Sequence:FRET
      quencher oligonucleotide for the detection of cyp1A1 mRNA

<400> SEQUENCE: 106
ctctgacaga tccca                                                    15
```

METHOD FOR DETECTING ANALYTES IN A SAMPLE

This is a 371 of PCT/EP2004/006344 filed 11 Jun. 2004.

The present invention pertains to a method for detecting analytes in a sample utilizing probes interacting with the analytes.

The detection and preferably quantitative analysis of nucleic acids is an important tool in the molecular biology laboratory. Examples are genetic tests, virus diagnostics, and analysis of polymorphisms. To date a number of DNA/RNA quantification systems have been developed. Typically, such quantification systems rely on an amplification step being performed exponentially (realized by Polymerase chain reaction (PCR), which is based on a specific, multiple turnover replication of the nucleic acid section to be identified) or linearly (realized by enzymatic turnover). Many detection and quantification systems rely on detecting analytes by labeled probes added to the sample in surplus. A part of the labeled probes binds to the analytes. When the binding reaction is complete, the unbound labeled probes are washed away, and the amount of analytes is quantified by the amount of bound labeled probes. Typically, such washing steps are indispensable to reduce the background signals stemming from unbound probes. However, washing steps are difficult to manage, if manageable at all, in an automated way. Automation, on the other hand, is a prerequisite for high throughput applications typical in mass diagnostics, drug testing and development, and alike situations.

An object of the present invention is to provide a sensitive method for the detection of low concentrations of nucleic acid analytes. The method should in particular be feasible (i) without additional amplification steps thereby allowing a direct detection of the analytes and (ii) in a homogeneous format without relying on washing or other separation steps.

In a first aspect, the object of the present invention is accomplished by a method for detecting analytes in a sample comprising the steps of providing a solid support, providing capture probes being bound or capable of binding to the solid support, which capture probes are also capable of binding to the analytes, thus concentrating the analytes on the solid support, providing detection probes which are capable of binding to the analytes, contacting the sample with the detection probes, the solid support and the capture probes, and detecting through use of confocal observation the analytes which are bound to the detection probes and further preferably concentrated on the solid support.

More specifically the method for detecting nucleic acid analytes comprises the steps of providing a solid support, in particular suspendable solid supports, providing capture probes being bound or capable of binding to the solid support(s), which capture probes are also capable of binding to the nucleic acid analytes, thus concentrating the nucleic acid analytes on the solid support(s), providing detection probes which are capable of binding to the nucleic acid analytes, contacting the sample with the detection probes, the solid support(s) and the capture probes, and detecting through use of confocal observation the nucleic acid analytes which are bound to the detection probes and further preferably concentrated on the solid support.

In general, the detection is preferably performed on sedimented suspendable solid supports.

It is understood that the above mentioned method steps of providing the solid support(s), the capture probes/capture oligonucleotides and the detection probes/detection oligonucleotides do not necessarily represent a sequential order.

According to the present invention, the analytes are detected through use of confocal observation, in particular confocal microscopy, confocal spectroscopy or confocal fluctuation analysis. Confocal observation confines detection of an illuminated object to a thin object plane. This is typically achieved by applying a pinhole in the image plane between detector and object lens. Radiation emitted from the object plane passes the pinhole which serves as a spatial filter and reaches the detector, whereas radiation from other planes is blocked. Consequently, background noise is substantially reduced. It is particularly preferred to acquire an image employing a confocal observation device (e.g. confocal laser scanning microscope or a confocal microscope with a Nipkow disk), thereby detecting the analytes which are bound to the detection probes.

It is an important feature of the present invention that the analytes are detected utilizing a solid support. Such a solid support is preferably a suspendable solid support. Typical suspendable solid supports are particles comprising polystyrene, other polymers, copolymers, terpolymers, or silica. Furthermore magnetic and superparamagnetic particles might be used. Such suspendable solid supports typically have a diameter of less than 200 µm, in particular less than 100 µm, more preferably less than 50 µm and even more preferably less than 10 µm. It is particularly useful to detect analytes bound to sedimented suspendable solid supports. Consequently, one may allow the suspendable solid support(s) to settle in the medium prior to detecting the analytes. Detecting analytes bound to sedimented suspendable solid supports is of particular benefit because a maximum of analytes is concentrated to the confocal detection plane. To achieve an effective sedimentation of the suspendable solid supports, the solid supports should have a density which is higher than the density of the medium in which they are suspended. It is preferred that the density of the suspendable solid supports is substantially higher than that of the medium, in particular higher than 1%, more preferably higher than 5%, even more preferably higher than 10%, most preferably higher than 20%, or even more. The medium might e.g. be an aqueous solution so that the density of the solid supports should be substantially higher than 1.0 g/ml. The invention typically employs a plurality of suspendable solid supports. For an effective detection, it is preferred that at least 5% of such supports have been allowed to settle when or prior to detecting the analytes indirectly bound to the suspendable solid supports (via their binding to the detection probes, the latter of which bind to the capture probes on the solid supports). It is even more preferred that at least 10%, or at least 20% or more particularly at least 50% of such supports have been allowed to settle when or prior to detecting the analyte. Advantages of using suspendable solid supports (such as beads) compared to non-suspendable solid supports (e.g. a chip or bottom of multi-well plates) are the following: 1. different bead sizes or shapes provide additional information and thereby allow the reliable detection of multiple targets (e.g. mRNA target "1" binds to 6 µm, mRNA target "2" binds to 10 µm beads), 2. instrumental insufficiencies (e.g. non-planar well bottom) which deteriorate an optical analysis are balanced out, 3. modular systems are more flexible (e.g. different use of beads and plates for different applications) 4. in combination with image analysis algorithms the use of beads (of uniform appearance) allows a differentiation between signal stemming from the beads and unwanted fluorescent contaminations (usually having a different morphology than beads). In addition, the use of suspendable solid supports with capture probes attached thereto facilitates the isolation of analytes from cell lysates; thereafter, the analytes bound to the suspendable solid supports (via the capture probes) can be reliable detected utilizing a confocal optical set-up.

The method of the invention is advantageous since no washing or other separation steps and no amplification of the signal are necessary. Consequently, in a preferred embodiment the method is indeed conducted in a homogeneous format. A direct detection of the analytes by the use of detection probes, in particular detection oligonucleotides, becomes possible. The signal intensity of the detection probe bound to the analyte, which is e.g. the intensity of emitted fluorescent light, is directly linked to the amount of analytes, omitting any amplifying turnover step. Consequently, the present invention which utilizes the advantages of confocal observation allows for a quantification of the analyte. This makes the method according to the present invention easy to handle, extremely robust and amenable to high throughput applications. Additional features are a dynamic range of 3 orders of magnitude, variability smaller than 15% and the feasibility to miniaturize the reaction volumes to about 25 µL, while reading and evaluating a 384 sample plate within about 10 minutes.

According to the invention, it becomes possible to determine in particular nucleic acid analytes which typically comprise at least two binding sites, one for a capture probe and another one for a detection probe. Usually, oligonucleotides are employed as such probes. In a preferred embodiment, a nucleic acid analyte is hybridized to a plurality of detection probes/detection oligonucleotides. This procedure significantly enhances the detection efficiency. The intensity of radiation stemming from a single nucleic acid analyte bearing a plurality of detection probes/detection oligonucleotides will be higher than from a single unbound detection probe/detection oligonucleotide. In case a plurality of nucleic acids are hybridized to capture probes on a solid support, their detection will be even more improved. In a further preferred embodiment, a nucleic acid analyte is hybridized to a plurality of capture probes/capture oligonucleotides. This procedure significantly enhances the detection specificity. The specificity of a hybridization reaction between a single nucleic acid analyte and a plurality of capture probes/capture oligonucleotides will be higher than the specificity based merely on a single capture probe/capture oligonucleotide. Consequently, in a preferred embodiment the method according to the present invention is carried out by conducting the following steps:

providing a suspendable solid support,
providing a plurality of different capture probes being bound or capable of binding to the suspendable solid support, which capture probes are also capable of binding to the analyte, thus concentrating the analyte on the suspendable solid support,
providing a plurality of different detection probes which are capable of binding to the analyte,
contacting the sample with the detection probes, the suspendable solid support and the capture probes, and
detecting through use of confocal observation the analyte bound to the detection probes.

One specific embodiment of this general strategy is depicted in FIG. 1.

It is preferred that the detection probes are labeled with a first reporter whereas the solid support(s) may be labeled with a second reporter different from the first reporter. The first and/or second reporter is/are preferably luminescent, in particular fluorescent. In an additional embodiment, the first and/or second reporter is/are (a) dye(s). The detection probes, in particular the detection oligonucleotides, are labeled with a first fluorescent dye and/or the solid support(s) is/are labeled with a second fluorescent dye. Typical dyes include, but are not limited to, rhodamine dyes such as rhodamine-6-G, tetramethylrhodamine or rhodamine green, oxazine dyes, fluorescein, and the like.

When detecting nucleic acid analytes, it is preferred that in a first step a hybrid between detection oligonucleotides and analytes is formed. This complex is bound to the solid support(s) via the hybridization of the analytes to capture oligonucleotides. The concentration of the detection oligonucleotides should not be the limiting factor in this first hybridization reaction. Therefore, the detection oligonucleotides are typically added to the sample in high amounts because the actual amount of analyte is usually unknown. After the hybridization reaction between detection oligonucleotides and analytes is completed, usually surplus detection oligonucleotides not being bound to the analytes are present. The emission of the first reporter of these unbound detection oligonucleotides is the main cause of background signal, deteriorating the reliability of analysis. According to the present invention, the detection of analytes bound to the detection oligonucleotides is performed through use of confocal observation. As explained above, confocal observation substantially reduces the background noise and thereby helps to detect the bound analytes even in the presence of a substantial surplus of detection oligonucleotides. To further improve the signal-to-background ratio, one may detect the analytes bound to the detection oligonucleotides in the presence of quenching oligonucleotides hybridizing to surplus detection oligonucleotides not being bound to the analytes and thereby quenching at least partially an emission of the first reporter of said surplus detection oligonucleotides. It is preferred that the hybrid between detection oligonucleotides and analyte has a higher melting temperature than a hybrid between a detection oligonucleotide and a quenching oligonucleotide. Therefore, the complete method can be conducted at two different temperatures so that competition of quenching oligonucleotides with the analytes can be avoided. The melting temperature of the hybrid between detection oligonucleotides and analyte is at least 1° C., more preferably at least 2° C., even more preferably at least 5° C. and most preferably at least 10° C. higher than the melting temperature of the hybrid between a detection oligonucleotide and a quenching oligonucleotide under test conditions. Generally speaking, contacting the sample with the detection oligonucleotides is performed under first hybridization conditions allowing the generation of a stable hybrid between detection oligonucleotides and analyte. Contacting the sample with the quenching oligonucleotides is performed under second hybridization conditions allowing the generation of a stable hybrid between surplus detection oligonucleotides not being bound to the analyte and quenching oligonucleotides. Said second hybridization conditions should not substantially destabilize the hybrid between detection oligonucleotides and analyte formed under said first hybridization conditions. This can be achieved via the choice of appropriate melting temperatures as explained above.

In a preferred embodiment, the capture probes, in particular the capture oligonucleotides, are covalently bound to the solid support. It is however alternatively also possible to utilize capture probes, in particular capture oligonucleotides, which are capable of binding to the solid support via affinity interaction. In this instance, the capture probes/capture oligonucleotides comprise a first affinity unit capable of binding to a second affinity unit attached to the solid support. As a typical example, the first affinity unit might be biotin and the second affinity unit might be streptavidin or avidin.

As mentioned above, a typical suspendable solid support may be a bead, a cell, a pollen, or a plurality thereof which preferably are allowed to settle prior to confocal analysis. According to the invention, the analyte is bound to the support via a capture probe. The capture probe of the invention may comprise a first portion bound to the support and a second portion capable of binding the analyte. Each support may comprise a multitude of capture probes.

However, it is also possible to utilize as a solid support the bottom of a sample carrier such as a slide or a titerplate. In this case, it is preferable to attach the capture probes covalently to discrete spots on such carrier or to attach the above mentioned second affinity unit thereto. The advantage of discrete spots is that the analyte is concentrated on a predefined spot, improving sensitivity compared to a uniform analyte distribution on the carrier bottom.

As already mentioned, the present invention may make use of a first reporter labeling the detection probes/detection oligonucleotides and a second reporter labeling the solid support(s). Typically, the first reporter labeling the detection probes/detection oligonucleotides differs from the second reporter labeling the solid support in its excitation wavelength and/or its emission wavelength. When choosing the reporters in such a way as to have different emission wavelengths (e.g. dyes emitting light at a wavelength of 565 nm for the first reporter and 690 nm for the second reporter; see examples below), these can be easily distinguished during detection. However, it is also possible to utilize reporters with different excitation wavelengths but the same emission wavelength. In this case, the first reporter and the second reporter are excited at different points in time and their emission is recorded correspondingly. Due to the time difference, the detected signal can be correlated to the different reporters. The difference in the excitation wavelength and/or emission wavelength between first and second reporter is typically at least 10 nm, preferably at least 20 nm, even more preferably at least 50 nm and most preferably at least 100 nm.

It is also preferred that the detection oligonucleotides comprise a linker sequence. This linker sequence links the sequence of the detection oligonucleotide complementary to the analyte with the first reporter. The capture oligonucleotides may also comprise a linker sequence, linking the sequence of the capture oligonucleotide complementary to the analyte with the affinity unit or the solid support (see e.g. the T15 linker mentioned in the examples below). The use of the linker sequences serves to spatially separate the first reporter labeling the detection oligonucleotides and the second reporter labeling the solid support(s) from each other (in the complex of detection oligonucleotides/analyte/capture oligonucleotides/solid support). Otherwise unfavorable interactions between these reporters may occur (e.g. FRET) which may reduce the signal emitted by the first reporter used to detect and quantify the analyte.

In an additional embodiment, the present invention is utilized in a multiplex format. At least two different analytes may be detected by providing at least two different sets of detection probes/detection oligonucleotides and at least two different sets of capture probes/capture oligonucleotides. The first set of detection oligonucleotides is complementary to the first analyte and the second set of detection oligonucleotides is complementary to the second analyte. The same applies to the capture oligonucleotides, accordingly. The different sets of detection probes/detection oligonucleotides are preferably labeled with different reporters. The reporters of one set are identical, have the same excitation wavelength and/or the same emission wavelength. Alternatively, the reporters of the detection probes/detection oligonucleotides are identical in the different sets. In this instance, it is preferred to utilize two different types of solid supports. The first analyte may be captured on a first type of solid support (such as a small bead). The second analyte may be captured on a second type of solid support (such as a large bead). The solid supports may be differentiated from each other by applying image analysis tools. Detecting the detection oligonucleotides bound to the first analyte can be conducted by utilizing a mask of the first type of solid supports, here small beads, whereas detecting the detection oligonucleotides bound to the second analyte can be conducted by utilizing a mask of the second type of solid supports, here large beads.

According to the present invention, the detection of the analytes bound to detection probes/detection oligonucleotides can be performed applying confocal imaging in combination with the generation of a mask. The solid support is labeled with a second reporter different from the one utilized to label the detection probes/detection oligonucleotides. An image is recorded at the emission wavelength of said second reporter. Thereafter, a mask is generated and applied to an image of the sample used for the above mentioned detection. It is preferred that the image recorded at the emission wavelength of the second reporter is recorded simultaneously with the image used for detecting the analytes bound to detection probes/detection oligonucleotides utilizing two detectors. This latter image is typically recorded at a wavelength different from the emission wavelength of the second reporter (see FIG. 5 below). The image of the sample used for detecting the analytes bound to detection probes/detection oligonucleotides typically is acquired at the emission wavelength of the first reporter. It is preferred to correct the image recorded at the emission wavelength of the second reporter in such a way that it spatially matches with the image used for detecting the analytes bound to detection probes/detection oligonucleotides. Alternatively, the latter image may be corrected to match the first image.

In another preferred embodiment, the quenching probes/quenching oligonucleotides comprises a quenching unit, said quenching unit preferably being a dye. In particular, the first reporter is a donor of a Förster resonance energy transfer (FRET) donor-acceptor-pair and the quenching unit is an acceptor of said donor-acceptor-pair. Alternatively, the quenching unit is a dark quencher which quenches at least partially the emission of the first reporter by dissipating the energy of the excited state of the first reporter into the environment.

When quantifying the analyte, such quantification may be performed by determining an amount of detection probes/detection oligonucleotides bound to the analyte. The signal stemming from the first reporter labeling such bound probes (in the complex of detection probe/analyte/capture probe/solid support) is related to the amount of the analyte. The amount of detection probes/detection oligonucleotides bound to the analyte may be expressed as the emission intensity emitted by the first reporter.

The method according to the present invention preferably comprises the additional step of determining an intensity of a background emission in the vicinity of the solid support and considering such intensity when determining the amount of analyte bound to detection probes/detection oligonucleotides.

In general, the detection probes may be aptameres, oligonucleotides, or antibodies. Analytes may be proteins or nucleic acids, in particular mRNA. The sample potentially comprising the analyte may be a cell lysate, in particular a crude cell lysate, or an in vitro prepared sample. The method according to the present invention is particularly useful in screening for potentially pharmaceutically active substances, in diagnostics, or in determining any potential side effects of drugs.

As already outlined above, in the case that the probe having the first reporter is a fluorescent probe and there are only a few analytes present it normally happens that the probe is present in an excess. Non-bound probe then emits fluorescent light which may cause a lowering of the sensitivity of the measurement. The use of confocal optics according to the present invention spatially limits the measurement volume to a very narrow well-defined focal plane thus reducing background signals. In addition, it is advantageous to add a quencher of a fluorescence of the first reporter unit and to reduce the background thereby. Due to utilizing quenching oligonucleotides complementary to the detection oligonucleotides and applying the above described specific hybridization conditions, it is possible to specifically quench the background fluorescence of the unbound detection oligonucleotides. This is done without quenching the signal fluorescence of the detection oligonucleotides bound to the analyte.

Additionally, the background signal can be eliminated by mathematical methods. For example, the background signal may be quantified in the vicinity of the solid support (though having sufficient distance to it) and subtracted from the signal of first reporter.

The probe having the first reporter is used for detecting the actual analyte, whereas the second reporter serves as marker for the solid support itself to which the analyte is bound, if present. Thus, the second reporter allows the localization of the solid support(s) and the subsequent generation of a mask which improves the accuracy of the measurement. In a preferred embodiment, the reporter are dyes having different absorption maxima and/or, if they are fluorescent dyes, different emission spectra. The skilled person readily understands how to choose the dyes according to the fluorescent filters in the confocal observation device which filters separate the excitation and/or emission bands of the two dyes.

In the following a brief description of the figures is given.

FIG. 1 depicts the result of a hybridization reaction utilizing detection oligonucleotides (DO), capture oligonucleotides (CO) and beads to detect a nucleic acid analyte. According to the present invention, the analyte bound to the detection oligonucleotides is detected through use of confocal observation. It is preferred that the confocal detection is performed on a sedimented bead.

Figure 6:
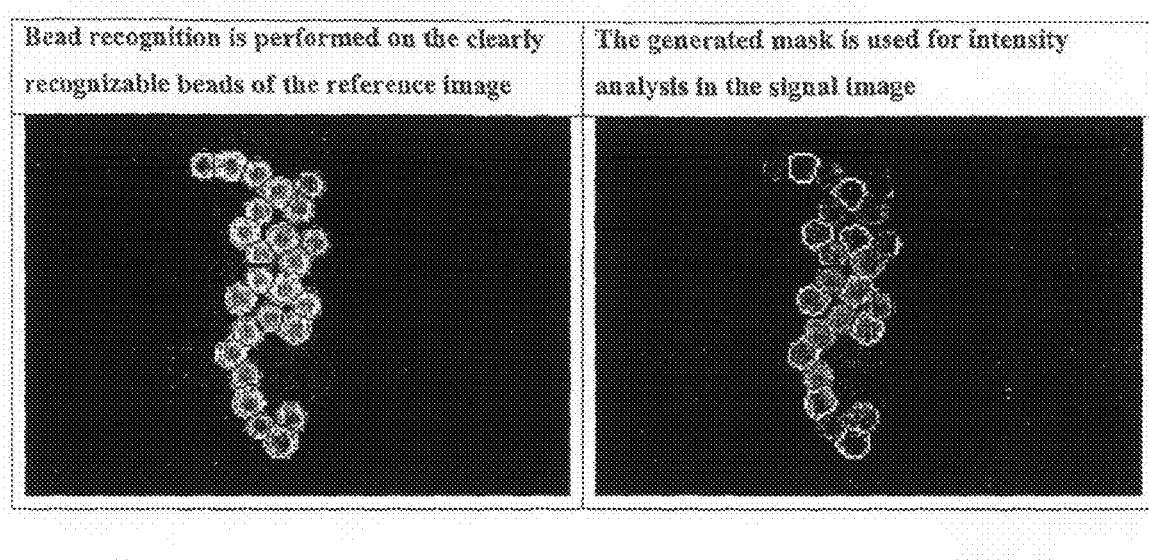

FIG. 6 shows a preferred embodiment of a strategy for image analysis. In the left hand figure, bead recognition is performed on clearly recognizable sedimented beads of the reference image. In the right hand figure, the generated mask is used for detecting the analyte bound to the sedimented beads via fluorescence intensity analysis in the signal image.

Figure 7:
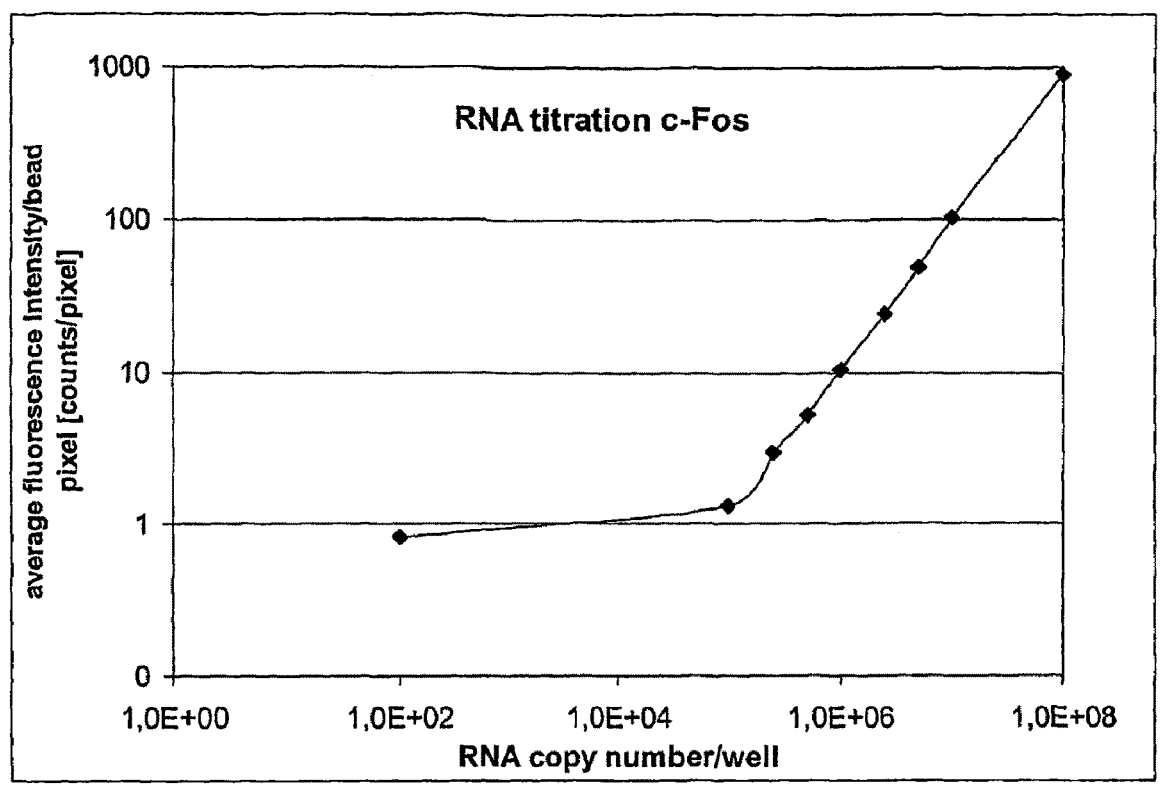

FIG. 7 depicts the results of c-fos RNA titration. Due to the logarithmic scale, the control is represented as $1*10^2$ copies (though in fact it does not contain any in vitro prepared c-fos RNA). The average fluorescence intensity per bead pixel relates to the amount of c-fos RNA analyte labeled with detection oligonucleotides and bound to the beads via the capture oligonucleotides.

Figure 8:
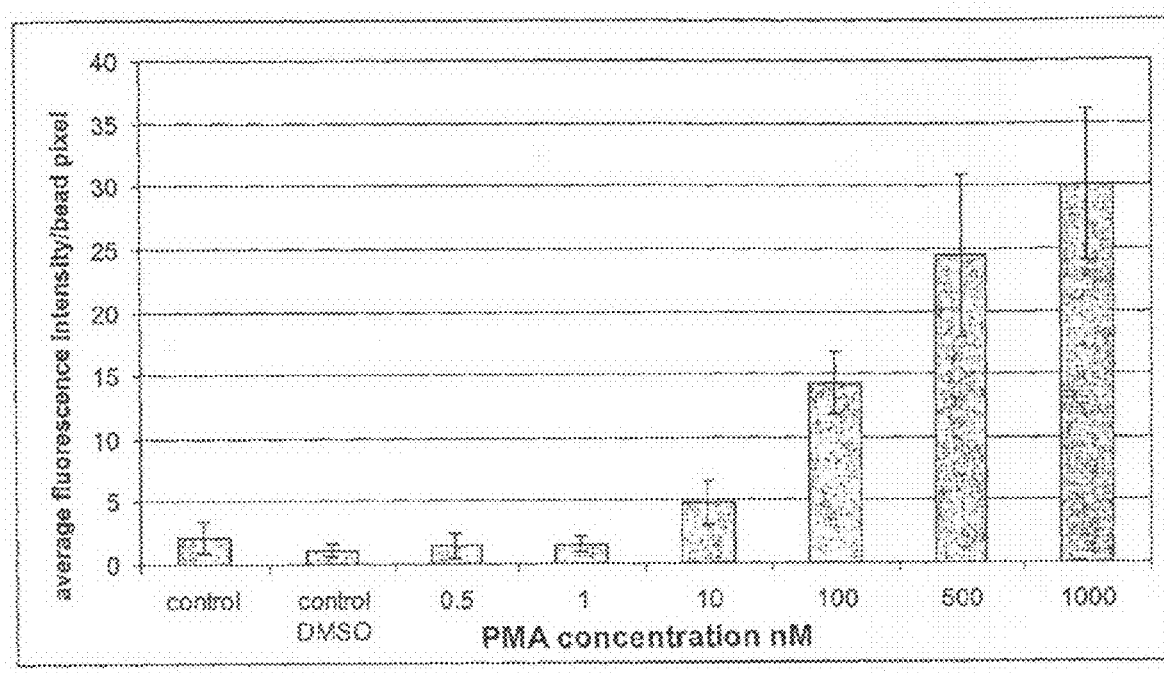

FIG. 8 shows the average fluorescence intensity per bead pixel at various PMA concentrations (c-fos experiments). The fluorescence intensity depicted in this FIG. 8 stems from emission of the detection oligonucleotides bound indirectly to the bead (via the analyte/capture oligonucleotide; see also FIGS. 1 and 2).

Figure 9:
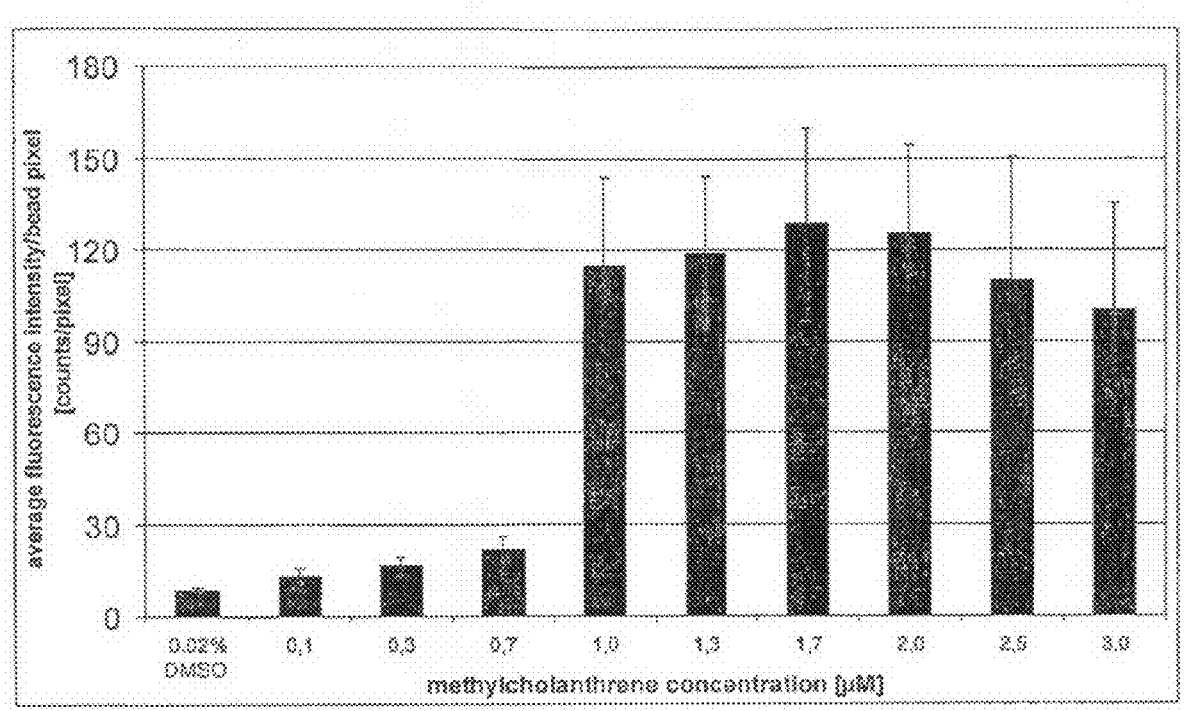

FIG. 9 shows the average fluorescence intensity per bead pixel at various 3-methylcholanthrene concentrations (cyp1A1 experiments). The fluorescence intensity depicted in this FIG. 9 stems from emission of the detection oligonucleotides bound indirectly to the bead (via the analyte/capture oligonucleotide; see also FIGS. 1 and 2). The result of measuring 32 wells per concentration of one sample plate is depicted (see also example 2).

The figures and various experiments conducted according to the present invention are explained in more detail in the following.

Figure 1:
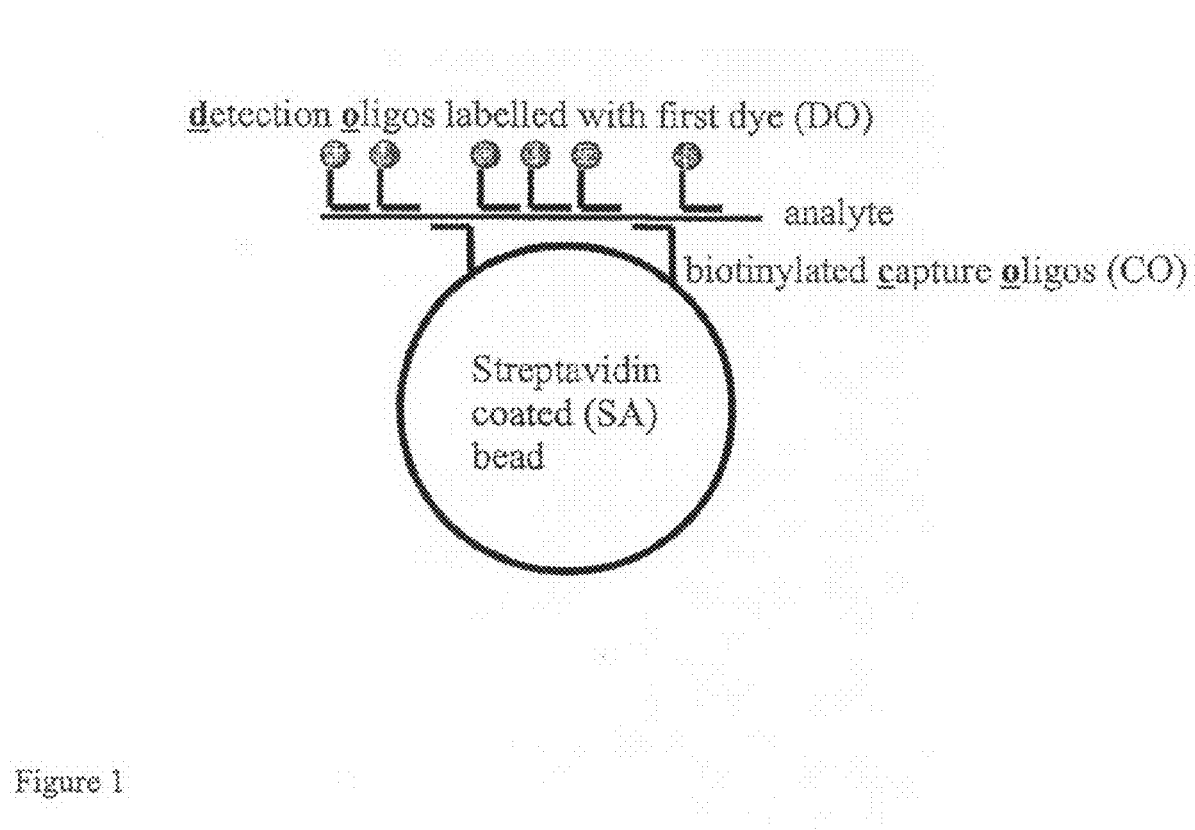

FIG. 1 depicts schematically that detection oligonucleotides (DO) labeled with a first dye are used to label the analyte nucleic acid. The resulting labeled complex is captured to streptavidin coated beads via hybridization of biotinylated capture oligonucleotides (CO). The capture oligonucleotides may alternatively be directly bound to a support (not depicted). The use of a bead or other solid support is advantageous because the analyte is concentrated thereon. It is particularly useful to detect sedimented beads applying confocal observation because a maximum of analytes is concentrated to the confocal detection plane.

Figure 2:
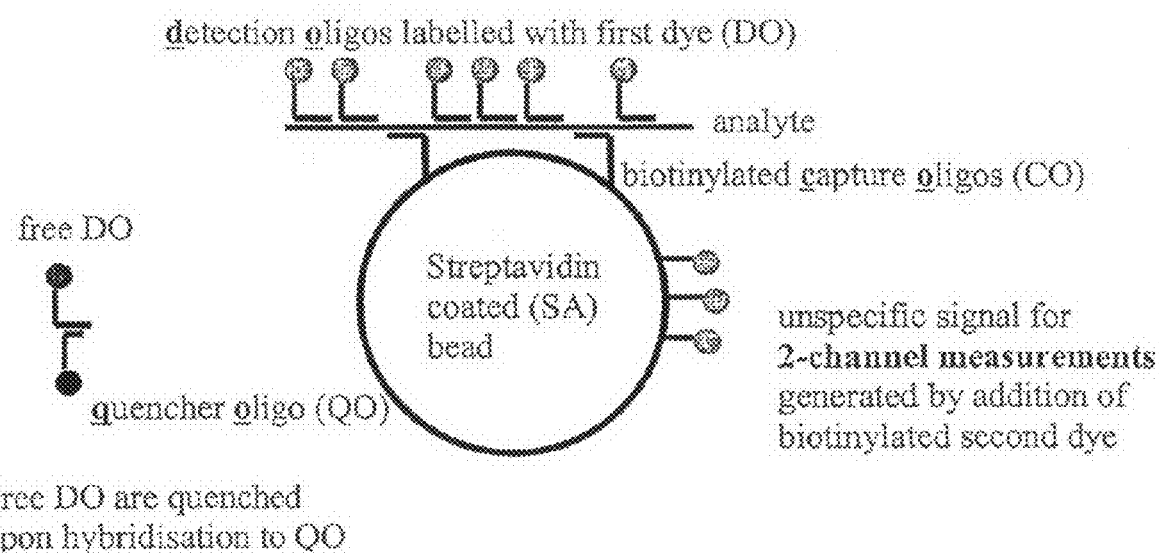
FIG. 2 depicts preferred measures taught by the present invention to additionally improve the sensitivity of the assay principle shown in FIG. 1.

FIG. 2 depicts measures that may be taken alone or in combination to reach an improved sensitivity of the method according to the present invention beyond that already achieved by the use of confocal observation techniques. The streptavidin coated beads may be labeled by biotinylated second dyes to allow their reliable detection independent of the analyte concentration. So called 2-channel measurements can be conducted by detecting both the signal of the labeled detection oligonucleotides bound to the analyte-CO-bead complex and the reference emission of the biotinylated second dye. In addition or alternatively, the background signal caused by unbound fluorescent detection oligonucleotides may be minimized using quencher oligonucleotides hybridizing to the free surplus detection oligonucleotides.

Figure 3:
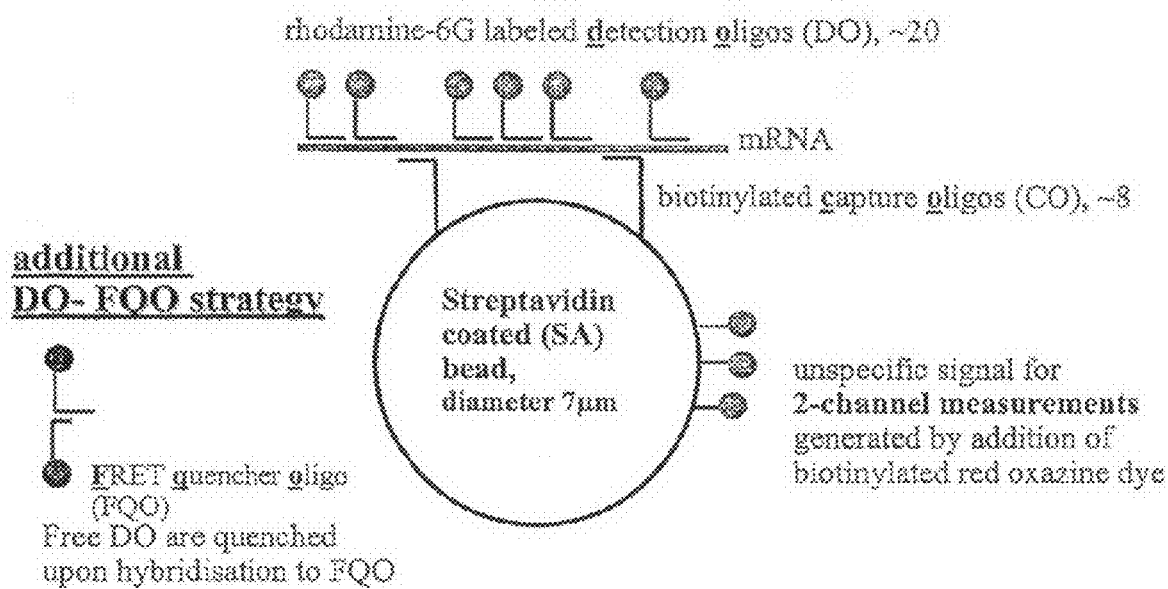
FIG. 3 shows an embodiment of the improved assay principle applying detection oligonucleotides labeled with rhodamine-6G, FRET quencher oligonucleotides and beads labeled with a red oxazine dye.

A further specific embodiment is depicted in more detail in FIG. 3. A number of about 20 detection oligonucleotides (DO) marked with the fluorescent dye rhodamine-6G is used to label the target mRNA, i.e. the analyte, specifically. The resulting fluorescent complex is captured to streptavidin coated beads via hybridization of biotinylated so-called capture oligonucleotides (CO). The fluorescence intensity on the beads may be recorded using high speed dual channel confocal imaging. The fluorescence intensity of the detection oligonucleotides bound indirectly to the beads (via analyte/CO-complex) is linearly related to the mRNA analyte concentration. To reach an improved sensitivity of the assay, additional steps can be taken according to the present invention, namely the unspecific labeling of the beads with a second color (such as biotinylated red oxazine dye) to allow their reliable detection independently of the RNA concentration. Furthermore, the background fluorescence caused by free surplus detection oligonucleotides can be minimized using FRET quencher oligonucleotides (FQO).

Figure 4:
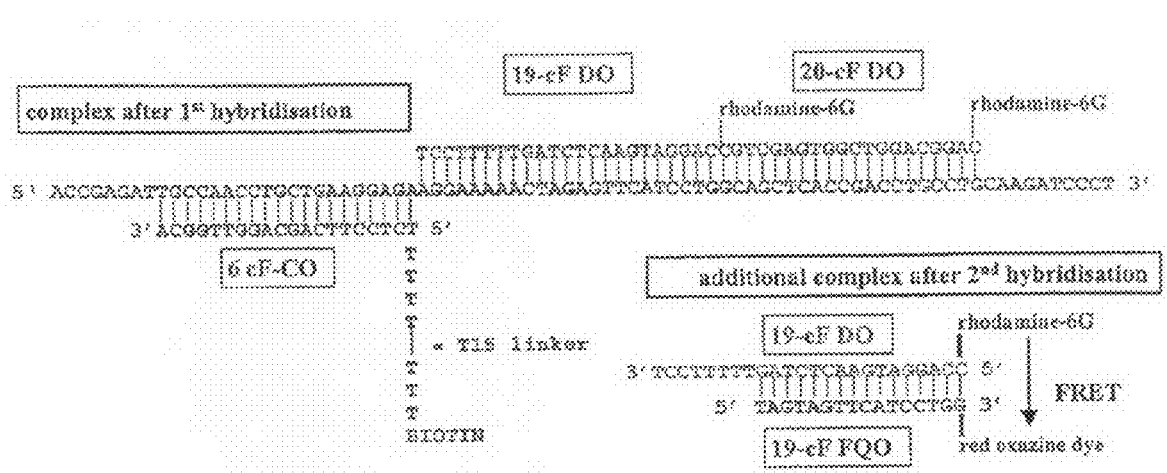
FIG. 4 depicts details of a preferred embodiment of the assay principle taught by the present invention for the detection of c-fos mRNA.

An even more detailed example is given in FIG. 4: The c-fos mRNA is labeled with two detection oligonucleotides (19 cF-DO and 20 cF-DO; for numbering of c-Fos oligonucleotides see Table 1). A biotinylated capture oligonucleotide (6 cf-CO) serves for binding to the bead (bead not depicted). In addition (lower right corner), the quenching of surplus DO (19 cF-DO) by its specific FQO (19 cF-FQO) is demonstrated.

In the following, the present invention is explained in more detail by the following examples. The general procedures described in the following section "Material and methods" are applicable to all examples.

Material and Methods

Cell Culture

HepG2 hepatoma cells were maintained in DMEM-F12 (Gibco, catalogue no. 31331-028), supplemented with 10% FCS (Gibco, catalogue no. 10500-064) at 37° C. and 5% $CO_2$. A549 cells were maintained in DMEM-F12 (Gibco, catalogue no. 31331-028), supplemented with 5% FCS (Gibco, catalogue no. 10500-064) at 37° C. and 5% $CO_2$.

Preparation of Lysis Buffer

The lysis buffer contained DEPC-treated water (RNase free) with 100 mM Tris/HCl pH 8.0, 10 mM EDTA pH 8.0, 0.5 M LiCl, 5 mM DTT, 1% (w/v) LiDS and 1 mg/ml Proteinase K (Roche Diagnostics, catalogue no. 1000144). A stock solution of the lysis buffer without Proteinase K was prepared and stored at −20° C., freshly prepared Proteinase K was added before each experiment. All chemicals were purchased in highest quality ("for molecular biology") from Sigma-Aldrich.

Streptavidin Coated Beads

Commercially available streptavidin coated polystyrene beads (SA beads) were applied. The beads were allowed to settle and detected via confocal imaging as set out below. The confocal detection plane is chosen in such a way that it lies in the plane of the sedimented beads bearing the bound analytes. As outlined above, the detection of sedimented beads applying confocal observation is particularly useful because a maximum of analytes is concentrated to the confocal detection plane.

Preparation of Biotinylated Red Oxazine Dye

A red oxazine dye was biotinylated using standard procedures. A 50 µM stock solution of the biotinylated red oxazine dye in DMSO was prepared.

Detection

Fully automated dual-channel confocal imaging was performed with two independent cooled CCD detectors. Excitation wavelengths were 532 nm and 633 nm, a dichroic beam splitter with 630 nm was used and emission filters were 565/50 nm and 690/40 nm. Laser power was 500 pW for both wavelengths, measured at the entrance of the objective. Exposure times were usually in the range of 500-1000 ms. 1-5 image pairs/well of a standard titerplate housing the sample were recorded, each image had a size of 445×336 µm.

In addition, correction images with appropriate dye solutions, pre-stained beads and dark images (detector noise) were recorded. In combination with appropriate algorithms these images were used for correction of assay images with regard to camera noise and irregularities of illumination. Furthermore, the image pairs from detectors 1 and 2 were spatially adjusted to achieve optimal overlap.

Evaluation

Images of the sample were acquired after sedimentation of the beads to be analyzed. An image of the sample was acquired at 565 nm by the first CCD detector. This image is called the signal image. At this wavelength, the emission of the detection oligonucleotides is seen. Therefore, in principle one can see the fluorescence emission of both the unbound detection oligonucleotides as well as the detection oligonucleotides bound specifically to the analyte (and consequently via the capture oligonucleotides to the beads). To distinguish these signals from each other, the present invention teaches in a preferred embodiment to minimize the emission of the unbound detection oligonucleotides by the use of complementary quencher oligonucleotides. The signal intensity on the beads is linear dependent on the analyte concentration, i.e. in the present example the mRNA concentration.

Figure 5:
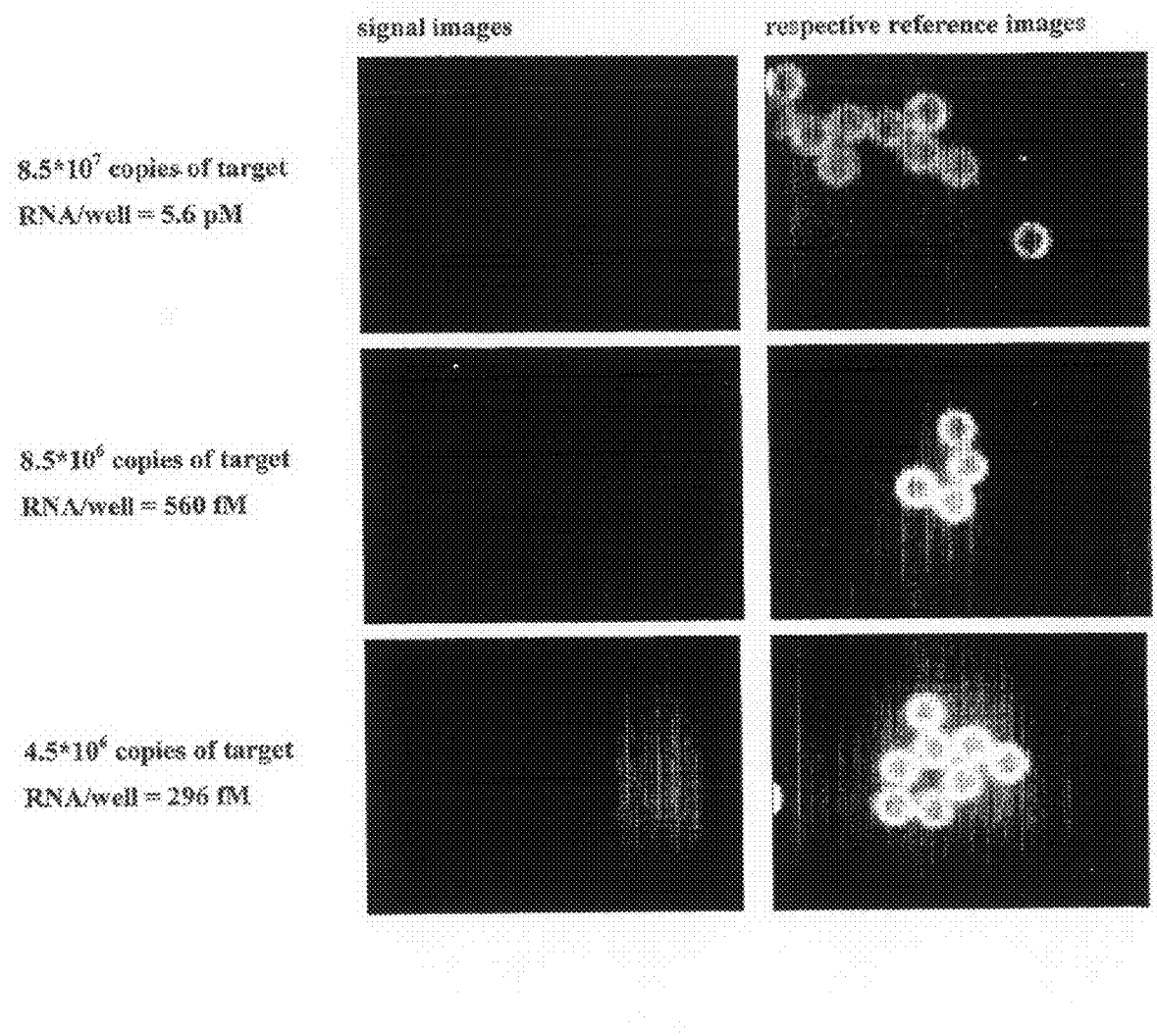
FIG. 5 shows signal images and reference images of sedimented beads at different concentrations of the target RNA analyte. The signal image was recorded at the emission wavelength of the first reporter labeling the detection oligonucleotides (565 nm), whereas the reference image was recorded at the emission wavelength of the second reporter labeling the beads (690 nm).

In addition, an image of the sample was acquired at 690 nm by the second CCD detector. This image is called the reference image. At this wavelength, the emission of the biotinylated red oxazine dye is seen. The fluorescence of the biotinylated red oxazine dye bound to the beads can be seen as a red ring in the reference image (see FIG. 6, left picture). This emission of the dyes bound to the beads can be distinguished from the background emission of the unbound biotinylated red oxazine dye through threshold techniques. This fluorescence intensity is constant and not dependent on the mRNA analyte concentration, see FIG. 5 for illustration. At extremely high mRNA concentrations it may become inversely related to the mRNA concentrations due to limited streptavidin binding sites, however, under physiological conditions and in the experiments presented here this was not the case.

The analysis of the images was performed with image analysis software as follows. Segmentation of the beads from the background was performed on a pixel-basis in the reference image. As can be seen in FIG. 6 (left picture), detected beads are marked by a ring. A mask of these rings corresponding to detected beads was generated from the reference image. This mask was applied to the signal image (see FIG. 6, right picture). Areas within the outer boundary of the ring were evaluated for fluorescence intensity stemming from the DO-analyte-CO complex bound to the bead. It was particularly advantageous to further reduce distorting background signals of free DO not completely quenched by determining the local background intensity in a circular region near every single bead in the signal image. Such local background intensity was then subtracted from the signal intensity.

The final result was the mean fluorescence intensity/bead pixel of the signal image. In general, the intensity was averaged over all correctly detected beads of the image. As already mentioned, images of sedimented beads were taken.

The sedimented beads were usually comprised in wells of micro- or nanotiter plates and in some cases, several images were taken of each well. In this instance, the intensity was averaged over all images of one well.

EXAMPLE 1

Detection of c-fos mRNA

Preparation of Oligonucleotides (DO, CO, UO and FQO)

A set of 19 detection oligonucleotides (DO) and 8 capture oligonucleotides (CO) was chosen. The DO were labeled with rhodamine-6G at the 5' terminus. The CO comprised a nucleotide sequence complementary to a sequence of the analyte, a T15-linker at the 5' terminus and biotin. The oligonucleotides were complementary to parts of the nucleotide sequence of the c-fos mRNA, had a minimal melting temperature Tm of 63° C. with a length varying between 17-26 nucleotides (nt), depending on GC-content. They covered a 676 nt long part of the c-fos mRNA (total length 1143 nt) between nucleotides 161 and 837 without intervening gaps. The DO and CO were chosen in such a way that they were not complementary to each other (DO and CO being complementary to each other would result in unspecific binding of DO to the beads via their direct binding to CO). 6 additional oligonucleotides had a too high degree of complementarity to others and were not labeled. These unlabeled oligonucleotides (UO) were nevertheless prepared and added to the hybridization solution to ensure that the respective part of the c-fos mRNA was completely covered and thus in a double-stranded, more stable conformation. The CO were chosen in a way that they were spaced relatively evenly between the DO. Furthermore, every DO was chosen to have the nucleotide A, C or T at the 5' terminus, because G is a known quencher of rhodamine-6G fluorescence.

In addition, a set of 19 FRET (Förster resonance energy transfer) quencher oligonucleotides (FQO) was prepared. These were complementary to the 5' terminal part of the respective DO, however, they were only 15 nt long, resulting in a lower minimal melting temperature Tm of ~42° C. They were labeled with a red oxazine dye at the 3' terminus. All oligonucleotides were synthesized according to standard procedures.

Stock solutions of oligonucleotides were prepared in TE-buffer (DEPC-treated water with 10 mM Tris-HCl, 1 mM EDTA pH 8.0) at a concentration of 100 μM and frozen at −80° C. DO-, CO-, UO- and FQO-mixtures were prepared (by adding equal amounts of each oligonucleotide solution) at a concentration of 100 μM. The DO-mixture comprised 19 different detection oligonucleotides, each individual oligonucleotide in this mixture was present at a concentration of 5.26 μM. For the FQO-mixture, the concentration of each individual oligonucleotide (FQO) was also 5.26 μM, whereas the individual concentration of each CO was 12.5 μM for CO-mixture and the individual concentration of each UO was 16.66 μM for UO-mixture.

The following table 1 shows a complete list of all oligonucleotides used for the detection of c-fos mRNA analyte. The position given below for the CO, DO and UO refers to the position on a DNA strand complementary to the mRNA analyte.

TABLE 1

List of oligonucleotides used for the detection of c-fos mRNA

| position | name | sequence |
|---|---|---|
| 8 Co (capture oligonucleotides) comprising a linker of 15 T-nucleotides (T15) and biotin attached to 5' terminus | | |
| 258-276 | 1 cF-CO | Biotin-5'-T15-ggctctggtctgcgatggg-3' |
| 277-296 | 2 cF-CO | Biotin-5'-T15-gggactccgaaagggtgagg-3' |
| 394-420 | 3 cF-CO | Biotin-5'-T15-ccttttctcttcttcttctggagataa-3' |
| 421-441 | 4 cF-CO | Biotin-5'-T15-attcctttcccttcggattct-3' |
| 528-548 | 5 cF-CO | Biotin-5'-T15-atctcggtctgcaaagcagac-3' |
| 549-568 | 6 cF-CO | Biotin-5'-T15-tctccttcagcaggttggca-3' |
| 633-655 | 7 cF-CO | Biotin-5'-T15-ccacagacatctcttctgggaag-3' |
| 656-676 | 8 cF-CO | Biotin-5'-T15-ccccagtcagatcaagggaag-3' |
| 19 DO (detection oligos) 5' labeled with rhodamine-6G (Rh6G) | | |
| 161-182 | 9 cF-DO | Rh6G-5'-atgaagttggcactggagacgg-3' |
| 183-200 | 10 cF-DO | Rh6G-5'-atggcagtgaccgtggga-3' |
| 201-219 | 11 cF-DO | Rh6G-5'-caggtccggactggtcgag-3' |
| 220-238 | 12 cF-DO | Rh6G-5'-cgggctgcaccagccactg-3' |
| 312-329 | 13 cF-DO | Rh6G-5'-ccagccctggagtaagcc-3' |
| 330-352 | 14 cF-DO | Rh6G-5'-ctcctgtcatggtcttcacaacg-3' |
| 353-371 | 15 cF-DO | Rh6G-5'-ccaatgctctgcgctcggc-3' |
| 372-393 | 16 cF-DO | Rh6G-5'-ctgttccaccttgccctcctg-3' |
| 462-478 | 17 cF-DO | Rh6G-5'-ccctcctccggttgcgg-3' |
| 479-501 | 18 cF-DO | Rh6G-5'-cgcttggagtgtatcagtcagct-3' |
| 569-592 | 19 cF-DO | Rh6G-5'-ccaggatgaactctagttttcct-3' |
| 593-611 | 20 cF-DO | Rh6G-5'-caggcaggtcggtgagctg-3' |
| 612-632 | 21 cF-DO | Rh6G-5'-cccaggtcatcagggatcttg-3' |
| 696-715 | 22 cF-DO | Rh6G-5'-aggcctcctcagactccggg-3' |

TABLE 1-continued

List of oligonucleotides used for the detection of c-fos mRNA

| position | name | sequence |
|---|---|---|
| 716-733 | 23 cF-DO | Rh6G-5'-tgaggagaggcagggtga-3' |
| 734-754 | 24 cF-DO | Rh6G-5'-agggcttgggctcagggtcat-3' |
| 755-775 | 25 cF-DO | Rh6G-5'-tgctcttgacaggttccactg-3' |
| 796-815 | 26 cF-DO | Rh6G-5'-aagtcatcaaagggctcggt-3' |
| 816-837 | 27 cF-DO | Rh6G-5'-cctggatgatgctgggaacagg-3' |

6 UO (unlabeled oligonucleotides)

| position | name | sequence |
|---|---|---|
| 239-257 | 28 cF-UO | 5'-gccacagaggagacgaggg-3' |
| 297-311 | 29 cF-UO | 5'-ccagcggaggggcg-3' |
| 442-461 | 30 cF-UO | 5'-catttggctgcagccatctt-3' |
| 502-527 | 31 cF-UO | 5'-ttctcatcttctagaggtctgtctc-3' |
| 677-695 | 32 cF-UO | 5'-gtggcaacctctggcaggc-3' |
| 776-795 | 33 cF-UO | 5'-cttcagctccatgctgctga-3' |

19 FQO (FRET quencher oligos) 3' labeled with red oxazine dye (RO)

| | name | sequence |
|---|---|---|
| 9 cF-DO | 9 cF-FQO | 5'-cag tgc caa ctt cat-3'-RO |
| 10 cF-DO | 10 cF-FQO | 5'-cac ggt cac tgc cat-3'-RO |
| 11 cF-DO | 11 cF-FQO | 5'-acc agt ccg gac ctg-3'-RO |
| 12 cF-DO | 12 cF-FQO | 5'-ggc tgg tgc agc ccg-3'-RO |
| 13 cF-DO | 13 cF-FQO | 5'-tta ctc cag ggc tgg-3'-RO |
| 14 cF-DO | 14 cF-FQO | 5'-aga cca tga cag gag-3'-RO |
| 15 cF-DO | 15 cF-FQO | 5'-agc gca gag cat tgg-3'-RO |
| 16 cF-DO | 16 cF-FQO | 5'-ggc aag gtg gaa cag-3'-RO |
| 17 cF-DO | 17 cF-FQO | 5'-gca acc gga gga ggg-3'-RO |
| 18 cF-DO | 18 cF-FQO | 5'-gat aca ctc caa gcg-3'-RO |
| 19 cF-DO | 19 cF-FQO | 5'-tag agt tca tcc tgg-3'-RO |
| 20 cF-DO | 20 cF-FQO | 5'-tca ccg acc tgc ctg-3'-RO |
| 21 cF-DO | 21 cF-FQO | 5'-ccc tga tga cct ggg-3'-RO |
| 22 cF-DO | 22 cF-FQO | 5'-agt ctg agg agg cct-3'-RO |
| 23 cF-DO | 23 cF-FQO | 5'-ccc tgc ctc tcc tca-3'-RO |
| 24 cF-DO | 24 cF-FQO | 5'-ctg agc cca agc cct-3'-RO |
| 25 cF-DO | 25 cF-FQO | 5'-aac ctg tca aga gca-3'-RO |
| 26 cF-DO | 26 cF-FQO | 5'-gcc ctt tga tga ctt-3'-RO |
| 27 cF-DO | 27 cF-FQO | 5'-cca gca tca tcc agg-3'-RO |

EXAMPLE 1a c-fos RNA Titration

In vitro Preparation of c-fos RNA

A549 cells were stimulated with a cytokine mixture (16.5 ng/ml IFN-γ, 41.7 ng/ml IL-1β and 25 ng/ml TNF-α) to induce c-fos mRNA expression. After 1 h the total RNA was isolated (QIAGEN, RNeasy Mini Protocol for RNA Cleanup). Then the 1143 nucleotides long coding sequence of c-fos (Genbank Accession-number K00650) was prepared by RT-PCR with two specific primers (forward primer: 5' GCG AAT TCC TCG GGC TTC AAC GCA GA 3', reverse primer: 5' ATG GAT CCC AGC GTG GGT GAG CTG A 3'). These primers contained an additional BamHI and EcoRI restriction site, respectively. The success of the PCR was verified via Agarose gelelectrophoresis and the PCR product was purified (QIAquick PCR Purification Kit). The PCR product was cloned into the vector pBluescript II KS(+/−) using the EcoRI and BamHI restriction sites. The resulting product was used for transformation of E. coli Top10 F' cells, several clones were picked and amplified. The constructs were verified by complete sequencing and amplified in E. coli-TOP 10 F' cells, purified (QIAquick PCR Purification Kit) and then linearized using BamHI. The linearized probe was used for in vitro transcription of RNA (Promega, Riboprobe System-T3/T7 Kit) using T3 RNA Polymerase. The resulting product was subjected to DNAse digestion and afterwards purified (QIAGEN, RNeasy Mini Protocol for RNA Cleanup). The RNA amount was determined (Agilent 2001 Bioanalyzer) to be 901 ng/µl=2.2 µM=1.35*$10^{12}$ copies RNA/µl (mean value of five independent measurements). The molecular weight of c-fos RNA is 401280 g/Mol.

Preparation of c-fos Control Lysate

3*$10^6$ HepG2 cells were seeded on a 10 cm tissue culture plate (Greiner bio-one, catalogue no. 664160) in 10 ml DMEM-F12 (Gibco, catalogue no. 31331-028) supplemented with 10% FCS (Gibco, catalogue no. 10500-064) and incubated at 37° C. and 5% $CO_2$. After 48 hours the medium was changed to DMEM (Sigma, catalogue no. D 5921) supplemented with 0.1% sterile filtered HSA (Sigma, catalogue no. A 1653). After incubation for 24 h the medium was changed to DMEM supplemented with 0.1% HSA and 0.02% DMSO. No PMA (Phorbol 12-myristate 13-acetate) was added so that no c-fos expression was induced. The cells were incubated for 1 h at 37° C. and 5% $CO_2$. Then the medium was removed and 5 ml lysis buffer was added, incubated for 15 min at 37° C. and 5% $CO_2$ and then mixed by repeated pipetting. This control lysate was stored at −20° C.

Assay Procedure

The in vitro prepared RNA was diluted with control lysate to yield the 8 different copy numbers/24 µl indicated in Table 2 below. A hybridization solution was prepared using the CO, DO and UO mixture solutions described above. Appropriate volumes were added to lysis buffer to yield a final concentration of 7 nM of each CO, DO and UO. Furthermore, the hybridization solution contained 3.7*$10^3$ SA beads/ml.

TABLE 2 c-fos RNA copy number/well

| copy number/24 µl (=copy number/well) | final RNA concentration |
|---|---|
| 1 * $10^8$ | 6.9 pM |
| 1 * $10^7$ | 692 fM |
| 5 * $10^6$ | 346 fM |
| 2.5 * $10^6$ | 173 fM |
| 1 * $10^6$ | 69 fM |
| 5 * $10^5$ | 34.6 fM |
| 2.5 * $10^5$ | 17.3 fM |
| 1 * $10^5$ | 6.9 fM |

Four 24 µl aliquots of each RNA dilution were transferred to the wells of a glass bottom, heat resistant measurement plate (NanoCarrier™96/30, Evotec Technologies), respectively. 4 additional wells were filled with 24 µl of control lysate. To each well, 1 µl of hybridization solution was added resulting in a final concentration of 0.28 nM of each DO, CO and UO. The final SA bead number per well was 3700. The measurement plate was placed into a humid incubator (Kendro, HERACELL 150/70 CO2 INKUBATOR VA 230V) and incubated at 53° C. After this first hybridization, a DO-analyte-CO-bead-complex was formed (see also the schematic drawing of FIG. 1).

A quencher solution was prepared using the FQO mixture solution and the stock solution of biotinylated red oxazine dye described above. Appropriate volumes were added to lysis buffer to yield a final concentration of 72.8 nM of each FQO and a final concentration of 1.3 µM of the biotinylated red oxazine dye. 1 µl of the quencher solution was added to each well of the measurement plate, resulting in a final concentration of 2.8 nM for each FQO and 50 nM of the biotinylated red oxazine dye. The measurement plate was again placed into a humid incubator and incubated at 35° C. After this second hybridization, a situation was achieved as depicted in FIG. 3. The emission of the free (unbound) detection oligonucleotides was quenched upon hybridization to the FRET quencher oligonucleotides. The biotinylated red oxazine dye served to generate a reference emission for the reliable detection of the beads. Then the plate was measured as described above. The measurement was performed on sedimented beads because under this condition a maximum of analytes is concentrated to a well-defined plane which can be reliably assessed applying confocal detection.

Results

The results are listed in Table 3 and depicted in FIG. 7. The RNA copy number is linearly related to the fluorescence signal intensity of the detection oligonucleotides bound via analyte/capture oligonucleotides to the beads over a range of three orders of magnitude, namely between $10^5$-$10^8$ copies of RNA/well. The lower detection limit is in the range of 5*$10^5$ copies of c-fos RNA or even below that can be distinguished reliably from the control. A linear fit of the data shown in FIG. 7 resulted in the equation y=1.06*$10^6$x−3.444. This calibration was used in example 1b for the calculation of mRNA copy number/cell.

TABLE 3

Results of c-fos RNA titration

| RNA copies/well | average fluorescence signal intensity/bead pixel | | | | | |
|---|---|---|---|---|---|---|
| | well 1 | well 2 | well 3 | well 4 | mean | standard deviation |
| 1.0 * $10^8$ | 912.8 | 1271.2 | 1010.1 | 943.9 | 1034.5 | 162.9 |
| 1.0 * $10^7$ | 95.3 | 86.3 | 84.0 | 81.1 | 86.7 | 6.1 |
| 5.0 * $10^6$ | 36.2 | 47.0 | 35.5 | 47.1 | 41.5 | 6.5 |
| 2.5 * $10^6$ | 24.5 | 24.2 | 22.1 | 20.6 | 22.8 | 1.8 |
| 1.0 * $10^6$ | 8.6 | 10.2 | 7.5 | 11.8 | 9.5 | 1.9 |
| 5.0 * $10^5$ | 5.1 | 4.5 | 6.4 | 6.9 | 5.7 | 1.1 |
| 2.5 * $10^5$ | 3.4 | 3.1 | 2.7 | 3.0 | 3.1 | 0.3 |
| 1.25 * $10^5$ | 2.3 | 1.4 | 1.5 | 1.8 | 1.7 | 0.4 |
| control ("1 * $10^3$") | 2.1 | 1.7 | 0.5 | 0.5 | 1.2 | 0.8 |

EXAMPLE 1b

Expression of c-fos mRNA in HepG2 cells

HepG2 cells were seeded at a density of 2*$10^6$ cells in 10 ml medium/plate (corresponding to 2*$10^5$ cells/ml) in nine 10 cm tissue culture plates (Greiner bio-one, catalogue no. 664160) in DMEM-F12 (Gibco, catalogue no. 31331-028) supplemented with 10% FCS (Gibco, catalogue no. 10500-064). The cells were incubated for 48 h at 37° C. with 5% $CO_2$. Then the medium was changed to DMEM (Sigma, catalogue no. D 5921) supplemented with 0.1%/0 sterile filtered HSA (Sigma, catalogue no. A 1653) and incubation was continued for 24 h at 37° C. with 5% $CO_2$. Then the cells were incubated with PMA (Phorbol 12-myristate 13-acetate, Sigma, catalogue no. P1585) for 1 h at 37° C. and 5% $CO_2$ to induce expression of c-fos. 500 µl of appropriate PMA dilutions in DMEM with 0.10% HSA were added, for final concentrations refer to table 4 below.

TABLE 4

PMA concentrations

| plate number | PMA concentration |
|---|---|
| 1 | 0 nM (control) |
| 2 | 0 nM, 0.1% DMSO (DMSO-control) |
| 3 | 0.5 nM |
| 4 | 1 nM |
| 5 | 10 nM |
| 6 | 100 nM |
| 7 | 500 nM |
| 8 | 1 µM |

One control plate was used for cell counting, the final cell number was 1.5*$10^7$ cells/plate. After 1 h the stimulation mixture was removed and the cells were lysed by addition of 5 ml lysis buffer/plate, resulting in a cell number of 3*$10^6$ cells/ml. Immediately after the addition of the lysis buffer the plates were put on ice and after 15 min stored at −20° C. for 24 h.

Assay Procedure

Eight 24 µl aliquots (each corresponding to 7.2*$10^4$ lysed cells) of the cell lysate of each PMA concentration were added to the wells of a heat-resistant glass bottom plate (Nanocarrier™ 384/30, Evotec Technologies), respectively. A hybridization solution was prepared using the CO, DO and UO mixture solutions described above. Appropriate volumes were added to lysis buffer to yield a final concentration of 7 nM of each CO, DO and UO. Furthermore, the hybridization solution contained $3.7*10^3$ SA beads/ml.

To each well, 1 µl of hybridization solution was added resulting in a final concentration of 0.28 nM of each DO, CO and UO. The final SA bead number per well was 3700. The measurement plate was placed into a humid incubator (Kendro, HERACELL 150/70 CO2 INKUBATOR VA 230V) and incubated at 53° C.

A quencher solution was prepared using the FQO mixture solution and the stock solution of biotinylated red oxazine dye described above. Appropriate volumes were added to lysis buffer to yield a final concentration of 72.8 nM of each FQO and a final concentration of 1.3 µM of the biotinylated red oxazine dye. 1 µl of the quencher solution was added to each well of the measurement plate, resulting in a final concentration of 2.8 nM for each FQO and 50 nM of the biotinylated red oxazine dye. The measurement plate was again placed into a humid incubator and incubated at 35° C. Then the plate was measured as described above. The measurement was performed on sedimented beads because under this condition a maximum of analytes is concentrated to a well-defined plane which can be reliably assessed applying confocal detection.

Results

The results are listed in Table 5 and depicted in FIG. 8.

With increasing PMA concentration (used to stimulate expression of c-fos mRNA) an increase in the average fluorescence intensity/bead pixel stemming from the detection oligonucleotide-mRNA analyte-capture oligonucleotide complex bound to the sedimented beads can be observed. Thus, PMA induced a strong increase in c-fos expression with an $EC_{50}$ of 484 nM. This is in the same order of magnitude as the $EC_{50}$ that can be estimated from published results (Northern Blot) (Arts, J., Grimbergen, J., Bosma, P. J., Rahmsdorf, H. J., and Kooistra, T. (1996). Role of c-Jun and proximal phorbol 12-myristate-13-acetate-(PMA)-responsive elements in the regulation of basal and PMA-stimulated plasminogen-activator inhibitor-1 gene expression in HepG2. Eur. J. Biochem. 241, 393-402). The z' values (Zhang J H, Chung T D, Oldenburg K R: A Simple Statistical Parameter for Use in Evaluation and Validation of High Throughput Screening Assays. *J Biomol Screen* 1999; 4:67-73) are positive down to 100 nM PMA, thus the reliable differentiation between control and stimulated sample down to a concentration of 100 nM PMA in high throughput screening (HTS) is possible.

Using the calibration of example 1a, the measured fluorescence intensity at 100 nM PMA equals a copy number of $3.03*10^6$ copies mRNA/well (corresponding to 24 µl of lysate). Taking into account that 24 µl of lysate contained $7.2*10^4$ lysed cells (see above), an average expression rate of 42 copies mRNA/cell was concluded.

TABLE 5

Results of c-fos mRNA expression in HepG2 cells

| PMA concentration [nM] | Mean average fluorescence signal intensity/ bead pixel | std | CV % | z' |
|---|---|---|---|---|
| 0 (control) | 2.15 | 1.31 | 60.68 | |
| 0 (control) | 1.09 | 0.51 | 47.17 | |

TABLE 5-continued

Results of c-fos mRNA expression in HepG2 cells

| PMA concentration [nM] | Mean average fluorescence signal intensity/ bead pixel | std | CV % | z' |
|---|---|---|---|---|
| DMSO) | | | | |
| 0.5 | 1.51 | 0.97 | 64.14 | −9.58 |
| 1 | 1.53 | 0.63 | 41.05 | −6.75 |
| 10 | 4.84 | 1.74 | 35.97 | −0.80 |
| 100 | 14.29 | 2.46 | 17.24 | 0.32 |
| 500 | 24.44 | 6.48 | 26.52 | 0.10 |
| 1000 | 30.03 | 5.97 | 19.89 | 0.33 |

EXAMPLE 2

Expression of cyp1A1 mRNA in HepG2 cells

Preparation of Oligonucleotides (DO, CO and FQO)

A set of 20 detection oligonucleotides (DO) and 8 capture oligonucleotides (CO) was chosen. The DO were labeled with rhodamine-6G at the 5' terminus. The CO comprised a nucleotide sequence complementary to a sequence of the analyte, a T15-linker at the 5' terminus and biotin. The oligonucleotides were complementary to parts of the nucleotide sequence of the cyp1A1 mRNA, had a minimal melting temperature Tm of 63° C. (with the exception of two unlabelled oligonucleotides with a Tm of 55° C.) with a length varying between 18-25 nt (with the exception of an UO with less than 18 nt), depending on GC-content. They covered a 686 nt long part of the cyp1A1 mRNA (total length 1539 nt) between nucleotides 405 and 1091 without intervening gaps. This region was chosen to avoid regions with high homology to cyp3A4 (e.g. nt 325-363). One short homologous region could not be avoided and was therefore covered by an unlabelled oligonucleotide (see below).

The DO and CO were chosen so as not to be complementary to each other (DO and CO being complementary to each other would result in unspecific binding of DO to the beads via their direct binding to CO). 3 oligonucleotides had a too high degree of complementarity to others and were not labeled. These unlabeled oligonucleotides (UO) were nevertheless prepared and added to the hybridization solution to ensure that the respective part of the cyp1A1 mRNA was completely covered and thus in a double-stranded, more stable conformation. A fourth unlabelled oligonucleotide was prepared to cover a region with a high degree of homology to cyp3A4 (31 Cy1-UO).

The CO were chosen in a way that they were spaced relatively evenly between the DO. Furthermore, every DO was chosen to have the nucleotide A, C or T at the 5' terminus, because G is a known quencher of rhodamine-6G fluorescence.

In addition, a set of 20 FRET quencher oligonucleotides (FQO) was prepared. These were complementary to the 5' terminal part of the DO, however, they were only 15 nt long, resulting in a lower minimal melting temperature Tm of 38° C. They were labeled with a red oxazine dye at the 3' terminus. All oligonucleotides were synthesized according to standard procedures.

Stock solutions of oligonucleotides were prepared in TE-buffer (DEPC-treated water with 10 mM Tris-HCl, 1 mM EDTA pH 8.0) at a concentration of 100 µM and frozen at −80° C. DO-, CO-, UO- and FQO-mixtures were prepared (by adding equal amounts of each oligonucleotide solution) at a concentration of 100 µM. The concentration of each individual oligonucleotide in these mixtures was 5 µM for DO-mixture and FQO-mixture, 12.5 µM for CO-mixture and 25 µM for UO-mixture.

The following table 6 shows a complete list of all oligonucleotides used for the detection of cyp1A1 mRNA analyte. The position given below for the CO, DO and UO refers to the position on a strand complementary to the mRNA analyte.

TABLE 6

List of oligonucleotides used for the detection of cyp1A1 mRNA

| position | Name | sequence |
|---|---|---|
| 8 CO (capture oligonucleotides) comprising a linker of 15 T-nucleotides (T15) and biotin attached to 5' terminus | | |
| 505-525 | 1 Cy1-CO | Biotin-5'-T15-ctgcaacgtgcttatcaggac-3' |
| 526-544 | 2 Cy1-CO | Biotin-5'-T15-caggccctgccatcagctc-3' |
| 633-656 | 3 Cy1-CO | Biotin-5'-T15-ttgactaggctaagcagttcttgg-3' |
| 657-679 | 4 Cy1-CO | Biotin-5'-T15-cctccccgaaattattattcagg-3' |
| 745-766 | 5 Cy1-CO | Biotin-5'-T15-cattcaggtccttgaaggcatt-3' |
| 767-791 | 6 Cy1-CO | Biotin-5'-T15-ttctgcatgaagctgtagaacttct-3' |
| 987-1008 | 7 Cy1-CO | Biotin-5'-T15-gttcatcaccaaatacatgagg-3' |
| 1033-1055 | 8 Cy1-CO | Biotin-5'-T15-ccaatcactgtgtctagctcctc-3' |
| 20 DO (detection oligos) 5' labelled with rhodamine-6G (Rh6G) | | |
| 405-422 | 9 Cy1-DO | Rh6G-5'-ccattctgggccaggcgc-3' |
| 423-445 | 10 Cy1-DO | Rh6G-5'-aggcaatggagaaacttttcagg-3' |
| 446-463 | 11 Cy1-DO | Rh6G-5'-ttgaggaggctgggtcag-3' |
| 464-485 | 12 Cy1-DO | Rh6G-5'-tgctcttccaggtagcaggagg-3' |
| 570-592 | 13 Cy1-DO | Rh6G-5'-tgacattggtcactgataccacc-3' |
| 593-611 | 14 Cy1-DO | Rh6G-5'-ccaaagcaaatggcacaga-3' |
| 612-632 | 15 Cy1-DO | RhGG-5'-tggttgtggtcatagcgccgg-3' |
| 680-699 | 16 Cy1-DO | Rh6G-5'-tgggtttccagagccaacca-3' |
| 700-722 | 17 Cy1-DO | Rh6G-5'-cgaagaatagggatgaactcagc-3' |
| 723-744 | 18 Cy1-DO | Rh6G-5'-cagggaagggttgggtaggtag-3' |

TABLE 6-continued

List of oligonucleotides used for the detection of cyp1A1 mRNA

| position | Name | sequence |
|---|---|---|
| 792-814 | 19 Cy1-DO | Rh6G-5'-ttttgtagtgctccttgaccatc-3' |
| 815-833 | 20 Cy1-DO | Rh6G-5'-atgtggcccttctcaaagg-3' |
| 834-856 | 21 Cy1-DO | Rh6G-5'-tcaggctgtctgtgatgtcccgg-3' |
| 857-878 | 22 Cy1-DO | Rh6G-5'-tgcttctcctgacagtgctcaa-3' |
| 879-898 | 23 Cy1-DO | Rh6G-5'-cattggcgttctcatccagc-3' |
| 899-922 | 24 Cy1-DO | Rh6G-5'-gatcttctcatctgacagctgga-3' |
| 923-946 | 25 Cy1-DO | Rh6G-5'-caaagaggtccaagacgatgttaa-3' |
| 947-967 | 26 Cy1-DO | Rh6G-5'-tgactgtgtcaaacccagctc-3' |
| 1009-1032 | 27 Cy1-DO | Rh6G-5'-ttggatctttctctgtaccctggg-3' |
| 1070-1091 | 28 Cy1-DO | Rh6G-5'-tgggatctgtcagagagccggg-3' |
| 4 UO (unlabelled oligonucleotides) | | |
| 486-504 | 29 Cy1-UO | 5'-ctcagcctccttgctcaca-3' |
| 545-569 | 30 Cy1-UO | 5'-acatacctgtaggggttaaagtgcc-3' |
| 968-986 | 31 Cy1-UO | 5'-ctccaggagatagcagttg-3' |
| 1056-1069 | 32 Cy1-UO | 5'-gccgccgtgacctg-3' |
| 20 FQO (FRET quencher oligos) 3' labeled with red oxazine dye (RO) | | |
| 9 Cy1-DO | 9 Cy1-FQO | 5'-cct ggc cca gaa tgg-3'-RO |
| 10 Cy1-DO | 10 Cy1-FQO | 5'-gtt tct cca ttg cct-3'-RO |
| 11 Cy1-DO | 11 Cy1-FQO | 5'-acc cag cct cct caa-3'-RO |
| 12 Cy1-DO | 12 Cy1-FQO | 5'-cta cct gga aga gca-3'-RO |
| 13 Cy1-DO | 13 Cy1-FQO | 5'-cag tga cca atg tca-3'-RO |
| 14 Cy1-DO | 14 Cy1-FQO | 5'-tgc cat ttg ctt tgg-3'-RO |
| 15 Cy1-DO | 15 Cy1-FQO | 5'-cta tga cca caa cca-3'-RO |
| 16 Cy1-DO | 16 Cy1-FQO | 5'-ggc tct gga aac cca-3'-RO |
| 17 Cy1-DO | 17 Cy1-FQO | 5'-cat ccc tat tct tcg-3'-RO |
| 18 Cy1-DO | 18 Cy1-FQO | 5'-ccc aac cct tcc ctg-3'-RO |
| 19 Cy1-DO | 19 Cy1-FQO | 5'-agg agc act aca aaa-3'-RO |
| 20 Cy1-DO | 20 Cy1-FQO | 5'-tga gaa ggg cca cat-3'-RO |
| 21 Cy1-DO | 21 Cy1-FQO | 5'-tca cag aca gcc tga-3'-RO |
| 22 Cy1-DO | 22 Cy1-FQO | 5'-ctg tca gga gaa gca-3'-RO |
| 23 Cy1-DO | 23 Cy1-FQO | 5'-atg aga acg cca atg-3'-RO |
| 24 Cy1-DO | 24 Cy1-FQO | 5'-cag atg aga aga tca-3'-RO |

TABLE 6-continued

List of oligonucleotides used for the detection of cyp1A1 mRNA

| position | Name | sequence |
|---|---|---|
| 25 Cy1-DO 25 | Cy1-FQO | 5'-tct tgg acc tct ttg-3'-RO |
| 26 Cy1-DO 26 | Cy1-FQO | 5'-ggt ttg aca cag tca-3'-RO |
| 27 Cy1-DO 27 | Cy1-FQO | 5'-cag aga aag atc caa-3'-RO |
| 28 Cy1-DO 28 | Cy1-FQO | 5'-ctc tga cag atc cca-3'-RO |

Expression of cyp1A1mRNA in HepG2 Cells

For experiment the cells were seeded at $1*10^4$ cells/50 µl per well in a 384 titerplate (Greiner; catalogue number 781091) in DMEM-F12 supplemented with 10% FCS. After 24 h of incubation at 37° C. and 5% $CO_2$ 10 µl of 3-methylcholanthrene (3-MC) in different concentrations was added for stimulation of cyp1A1 expression for 24 h at 37° C. and 5% $CO_2$. The final 3-MC concentrations were 0 µM (control), 0 µM+0.02% DMSO (DMSO-control), 0.1 µM, 0.3 µM, 0.7 µM, 1 µM, 1.3 µM, 1.7 µM, 2 µM, 2.5 µM, 3 µM and 3.5 µM. Each concentration was present 32 times.

3-MC stock solution was prepared with DMSO and diluted with DMEM-F12+10% FCS, the final DMSO concentration in the wells never exceeded 0.02%. After 24 h the stimulation mix was removed, 50 µl of lysis buffer were added to each well and incubation took place for 15 min at 37° C., 5% $CO_2$. Then the plate was frozen at −20° C. for three days until the assay procedure was performed.

Assay Procedure

24 µl of the cell lysate from each well of the cell culture plate was transferred to a corresponding well of a glass bottom measurement plate (Nanocarrier™ 384/30, Evotec Technologies). A hybridization solution was prepared using the CO, DO and UO mixture solutions described above. Appropriate volumes were added to lysis buffer to yield a final concentration of 7 nM of each CO, DO and UO. Furthermore, the hybridization solution contained $3.7*10^3$ SA beads/ml.

To each well, 1 µl of hybridization solution was added resulting in a final concentration of 0.28 nM of each DO, CO and UO. The final SA bead number per well was 3700. The measurement plate was placed into a humid incubator and incubated at 53° C.

A quencher solution was prepared using the FQO mixture solution and the stock solution of biotinylated red oxazine dye described above. Appropriate volumes were added to lysis buffer to yield a final concentration of 72.8 nM of each FQO and a final concentration of 1.3 µM of the biotinylated red oxazine dye. 1 µl of the quencher solution was added to each well of the measurement plate, resulting in a final concentration of 2.8 nM for each FQO and 50 nM of the biotinylated red oxazine dye. The measurement plate was again placed into a humid incubator and incubated at 35° C. Then the plate was measured as described above. Again, the measurement was performed on sedimented beads because under this condition a maximum of analytes is concentrated to a well-defined plane which can be reliably assessed applying confocal detection.

Result

The result is depicted in FIG. 9. With increasing 3-MC concentration (used to stimulate expression of cyp1A1 mRNA) an increase in the average fluorescence intensity/bead pixel stemming from the detection oligonucleotide-mRNA analyte-capture oligonucleotide complex bound to beads can be observed. The $EC_{50}$ determined for the plate was 0.8 µM; this result is similar to published results, (see e.g Delescluse, C., Ledirac, N., de Sousa, G., Pralavorio, M., Botta-Fridlund, D., Letreut, Y., and Rahmani, R. (1997), Comparative study of Cyp1A1 induction by 3-methylcholanthrene in various human hepatic and epidermal cell types. Toxicology in Vitro 11, 443-450). From a Northern Blot in this publication an $EC_{50}$ of ~0.5 µM can be roughly estimated, this is in excellent agreement with the present result.

The invention claimed is:

1. A method for detecting at least two different first and second analytes in a sample comprising the steps of
providing at least two different types of suspendable solid supports including a first type of solid support for capturing the first analyte and a second type of solid support for capturing the second analyte, the solid supports being suspended in a medium and having different sizes or shapes,
providing at least two different sets of capture probes bound or capable of binding to the solid supports, including a first set of capture probes capable of binding to the first analyte and a second set of capture probes capable of binding to the second analyte, thus concentrating the analytes on the solid supports,
providing detection probes which are capable of binding to the analytes,
contacting the sample with the detection probes, the solid supports and the capture probes,
detecting by confocal observation the presence or absence of the analytes bound to the detection probes, wherein at least 10% of the suspendable solid supports has been allowed to settle during or prior to the detecting step.

2. The method of claim 1 wherein at least 20% of the suspendable solid supports has been allowed to settle during or prior to the detecting step.

3. The method of claim 1 wherein at least 50% of the suspendable solid supports has been allowed to settle during or prior to the detecting step.

4. The method according to claim 1 wherein the confocal observation is by confocal microscopy, confocal spectroscopy, or confocal fluctuation analysis.

5. The method according to claim 1 wherein the confocal observation (a) is by laser scanning confocal microscopy or (b) employs a Nipkow disk.

6. The method according to claim 1 wherein confocal observation comprises acquiring an image, thereby detecting the analytes which are bound to the detection probes.

7. The method according to claim 1 being conducted in a homogeneous format.

8. The method according to claim 1 wherein the detection probes are labeled with a first reporter.

9. The method according to claim 1 wherein the detection probes are labeled with a luminescent first reporter.

10. The method according to claim 1 wherein the detection probes are oligonucleotides.

11. The method according to claim 1 wherein the capture probes are oligonucleotides.

12. The method according to claim 1 wherein the capture probes are covalently bound to the solid support.

13. The method according to claim 1 wherein the capture probes are bound or capable of binding to the solid support via affinity interaction.

14. The method according to claim 13 wherein the capture probes comprise a first affinity unit bound or capable of binding to a second affinity unit attached to the solid support.

15. The method of claim 14, the first affinity unit being biotin and the second affinity unit being streptavidin or avidin.

16. The method according to claim 1 wherein the analytes are nucleic acids.

17. The method according to claim 1 wherein each suspendable solid support is less than about 200 µm in diameter.

18. The method according to claim 1, wherein each suspendable solid support is less than about 50 µm in diameter.

19. The method according to claim 1, wherein each suspendable solid support is less than about 10 µm in diameter.

20. The method according to claim 1 wherein each suspendable solid support has a density higher than the density of the medium.

21. The method according to claim 20 wherein the medium is an aqueous solution and the density of each solid support is higher than 1.0 g/ml.

22. The method according to claim 1 wherein each suspendable solid support is a bead.

23. The method according to claim 1 wherein the different sets of detection probes are labeled with different first reporters.

24. The method according to claim 23 wherein the first reporters of one set of detection probes are identical.

25. The method according to claim 1 further comprising the step of quantifying the analytes.

26. The method according to claim 25 wherein the quantification of the analytes is performed by determining the amount of detection probes bound to the analytes.

27. The method according to claim 26 wherein the amount of detection probes bound to the analytes is expressed as the emission intensity emitted by the first reporters.

28. The method according to claim 26 further comprising the step of determining intensity of background emission in the vicinity of the solid support and considering the intensity when determining the amount of detection probes bound to the analytes.

29. The method according to claim 1 further comprising adding a potentially pharmaceutically active substance or a known drug to a cellular sample and analyzing whether the substance or drug induces, inhibits, or otherwise modulates the detection of the analytes.

30. The method according to claim 1 wherein the sample is a modified or unmodified crude cell lysate or an in vitro prepared sample.

31. The method according to claim 1 for use in screening for potentially pharmaceutically active substances, in diagnostics, or in determining any potential side effect of drugs.

32. The method according to claim 1 wherein each capture probe binds to a different binding site of each analyte.

33. The method according to claim 1 wherein each detection probe binds to a different binding site of each analyte.

* * * * *